United States Patent
Chang

(10) Patent No.: US 12,089,757 B2
(45) Date of Patent: Sep. 17, 2024

(54) ANTI-TREMOR TOOL

(71) Applicant: iCanInnoTech Co., Ltd., Taipei (TW)

(72) Inventor: Di-Jie Chang, Taipei (TW)

(73) Assignee: iCanInnoTech Co., Ltd., Taipei (TW)

( * ) Notice: Subject to any disclaimer, the term of this patent is extended or adjusted under 35 U.S.C. 154(b) by 0 days.

(21) Appl. No.: 17/039,116

(22) Filed: Sep. 30, 2020

(65) Prior Publication Data

US 2021/0007519 A1    Jan. 14, 2021

Related U.S. Application Data

(63) Continuation of application No. PCT/US2020/025325, filed on Mar. 27, 2020.

(30) Foreign Application Priority Data

Mar. 29, 2019    (TW) .................................. 108111430

(51) Int. Cl.
  *A47G 21/04*    (2006.01)
  *A47G 21/02*    (2006.01)
  (Continued)

(52) U.S. Cl.
  CPC .............. *A47G 21/04* (2013.01); *A47G 21/02* (2013.01); *A47G 21/08* (2013.01); *A61H 1/00* (2013.01);
  (Continued)

(58) Field of Classification Search
  CPC ........ A47G 21/02; A47G 21/04; A47G 21/08; A47G 2200/046; A47G 2200/106;
  (Continued)

(56) References Cited

U.S. PATENT DOCUMENTS 4,035,865 A * 7/1977 McRae .................. B25G 1/102
                                                        16/426
4,386,448 A * 6/1983 Kohn ..................... A47G 21/08
                                                        16/441
(Continued)

FOREIGN PATENT DOCUMENTS

CN          203646979 U      6/2014
CN          105212643 B     11/2016
(Continued)

OTHER PUBLICATIONS

International Search Report and Written Opinion dated Jul. 29, 2020 for International Application No. PCT/US2020/025325.

*Primary Examiner* — Jason Daniel Prone
(74) *Attorney, Agent, or Firm* — Winston Hsu

(57) ABSTRACT

An anti-tremor device including a tool unit, a carrying portion, and an anti-tremor module is disclosed. The tool unit is coupled or mounted on the carrying portion. The anti-tremor module is disposed on the carrying portion. The anti-tremor module includes a rotary transmission mechanism and a control module. The control module includes a sensing unit and a control unit. The sensing unit is coupled to the control unit, and the control module is coupled to the rotary transmission mechanism. When the sensing unit senses the tremor of the carrying portion, the control unit controls the rotary transmission mechanism to increase the inertia of the anti-tremor module to eliminate or reduce the tremor of the carrying portion.

11 Claims, 11 Drawing Sheets

(51) Int. Cl.
*A47G 21/08* (2006.01)
*A61H 1/00* (2006.01)

(52) U.S. Cl.
CPC .. *A47G 2200/046* (2013.01); *A47G 2200/106* (2013.01); *A47G 2200/22* (2013.01); *A47G 2400/08* (2013.01)

(58) Field of Classification Search
CPC .. A47G 2200/22; A47G 2400/08; A61H 1/00; B43L 15/00; B43K 23/004; B43K 23/008; A61B 5/1101; A61B 5/4082; A61B 5/6887; A46B 5/021; B25G 1/102; A61F 4/00
USPC ............ 30/142, 147–150, 322–328; 600/595
See application file for complete search history.

(56) References Cited

U.S. PATENT DOCUMENTS

| | | | |
|---|---|---|---|
| 4,523,781 A | 6/1985 | Brody | |
| 4,719,702 A * | 1/1988 | Hoffman | A47G 21/02 30/326 |
| 5,597,189 A * | 1/1997 | Barbee, Sr. | A61F 4/00 623/65 |
| 5,713,104 A * | 2/1998 | Giampaolo, Jr. | A47G 21/08 16/422 |
| D401,493 S * | 11/1998 | Lin | D8/107 |
| 5,860,190 A * | 1/1999 | Cano | A47G 21/02 30/327 |
| 5,950,280 A * | 9/1999 | Taylor | A47G 21/08 30/324 |
| 6,458,089 B1 * | 10/2002 | Ziv-Av | A61B 5/1101 600/595 |
| D527,187 S * | 8/2006 | Ramelli | D4/138 |
| 7,438,726 B2 * | 10/2008 | Erb | A61F 2/583 623/57 |
| D619,414 S * | 7/2010 | Williams | D7/401.2 |
| D658,017 S * | 4/2012 | Roberts | D7/401.2 |
| 8,308,664 B2 * | 11/2012 | Pathak | A47G 21/02 600/595 |
| 8,387,263 B1 * | 3/2013 | Roberts | A47G 21/04 30/324 |
| 8,468,700 B2 * | 6/2013 | Wilson | B25G 1/102 30/147 |
| 8,769,832 B1 * | 7/2014 | Joyner | A47G 21/02 30/322 |
| 8,844,099 B2 * | 9/2014 | Puig | B25G 1/102 16/422 |
| 9,044,853 B2 * | 6/2015 | Phui | B25G 1/102 |
| D760,538 S * | 7/2016 | Dodd | D7/401.2 |
| 9,818,310 B2 * | 11/2017 | Pathak | A47G 21/02 |
| D807,693 S * | 1/2018 | Obmaces | D7/401.2 |
| 9,925,034 B2 * | 3/2018 | Pathak | A61F 4/00 |
| 9,943,430 B2 * | 4/2018 | Pathak | A47G 21/02 |
| 10,058,445 B2 * | 8/2018 | Pathak | A47G 21/02 |
| 10,070,807 B2 * | 9/2018 | Shoeb | A47G 21/02 |
| 10,195,097 B1 * | 2/2019 | Cimo | A61H 1/00 |
| 10,219,930 B2 | 3/2019 | Pathak et al. | |
| 10,264,904 B1 * | 4/2019 | Kim | A47G 21/04 |
| 10,271,770 B2 * | 4/2019 | Pathak | A61F 4/00 |
| 10,368,669 B2 * | 8/2019 | Pathak | A47G 21/08 |
| 10,420,663 B2 * | 9/2019 | Pathak | A47G 21/02 |
| 10,420,693 B2 * | 9/2019 | Schubert | A61H 23/02 |
| 10,449,663 B2 * | 10/2019 | Martin | B25G 1/102 |
| 10,455,963 B2 * | 10/2019 | Pathak | A47G 21/08 |
| D865,367 S * | 11/2019 | Courtney | D4/104 |
| 10,497,279 B2 * | 12/2019 | Pathak | A47G 21/02 |
| 10,507,155 B1 * | 12/2019 | Cimo | A61H 1/00 |
| D873,609 S * | 1/2020 | Dodd | D7/401.2 |
| 10,532,465 B2 * | 1/2020 | Pathak | A47G 21/02 |
| 10,583,061 B2 * | 3/2020 | Pathak | A47G 21/02 |
| 10,600,596 B2 * | 3/2020 | Pathak | A47G 21/02 |
| 10,758,388 B2 * | 9/2020 | Pathak | A47G 21/02 |
| 10,849,776 B2 * | 12/2020 | Wu | A47G 21/08 |
| 10,851,867 B2 * | 12/2020 | Pathak | A47G 21/04 |
| D914,442 S * | 3/2021 | Andrea | D7/401.2 |
| D917,227 S * | 4/2021 | Yen | D7/401.2 |
| D917,964 S * | 5/2021 | Yen | D7/401.2 |
| 11,058,598 B2 * | 7/2021 | Pathak | A47G 21/02 |
| 11,097,427 B2 * | 8/2021 | Liu | A61B 5/1121 |
| 11,191,377 B2 * | 12/2021 | Jensen | A47G 19/2266 |
| D951,014 S * | 5/2022 | DeMumbrum | D7/401.2 |
| 2006/0025711 A1 * | 2/2006 | Bell | A61F 5/0118 602/21 |
| 2007/0209161 A1 * | 9/2007 | Neering | A47G 21/08 30/322 |
| 2012/0167348 A1 * | 7/2012 | Adams | B25G 1/102 16/426 |
| 2015/0310763 A1 * | 10/2015 | Miller | A46B 5/021 434/260 |
| 2016/0316948 A1 | 11/2016 | Marciano | |
| 2017/0157774 A1 | 6/2017 | Pathak et al. | |
| 2017/0290451 A1 * | 10/2017 | Flesher | A47G 21/02 |
| 2018/0005545 A1 | 1/2018 | Pathak et al. | |
| 2018/0058536 A1 * | 3/2018 | Pathak | A47G 21/04 |
| 2018/0133890 A1 | 5/2018 | Martin | |
| 2019/0151129 A1 * | 5/2019 | Pathak | A47G 21/02 |
| 2020/0015610 A1 * | 1/2020 | Pathak | A47G 21/08 |
| 2021/0298982 A1 * | 9/2021 | Pathak | A47G 21/02 |
| 2021/0369478 A1 * | 12/2021 | Campeau-Lecours | A47G 21/08 |

FOREIGN PATENT DOCUMENTS

| | | | | |
|---|---|---|---|---|
| JP | 2008067936 A | * | 3/2008 | ............ A47G 21/04 |
| JP | 2017023752 A | * | 2/2017 | ............ A47G 21/08 |
| JP | 2020163145 A | * | 10/2020 | ............ A47G 21/02 |
| TW | M43327201 | | 7/2012 | |
| WO | WO 2014/113813 A1 | | 7/2014 | |
| WO | WO-2020205557 A1 | * | 10/2020 | ............ A47G 21/02 |

\* cited by examiner

ANTI-TREMOR TOOL

CROSS-REFERENCE TO RELATED APPLICATION

This application is a bypass continuation under 35 U.S.C. § 111(a) of International App. No. PCT/US2020/025325 filed on Mar. 27, 2020 which claims priority to Taiwan App. No. 108111430 filed on Mar. 29, 2019, each of which is hereby incorporated herein by reference in its entirety.

TECHNICAL FIELD

The invention relates to an anti-tremor tool, in particular to an anti-tremor tool including an anti-tremor device or an auxiliary holding device.

BACKGROUND OF THE TECHNOLOGY

Tremor is a disease in medicine that includes resting tremor and intention tremor. A common symptom of tremor is uncontrollable hand tremor.

Limb tremor is one of the main symptoms of patients with Parkinson's disease. Some patients with severe tremors even have difficulty holding the tableware steadily, making it difficult to eat on their own and seriously affecting the quality of their life.

In order to enable patients with hand tremor to eat on their own, there is tableware with anti-tremor functions developed for patients with hand tremors. Generally, the traditional anti-tremor tableware is made bigger and heavier, so that the patients can hold it more stably, but the anti-tremor effect is limited. Common anti-tremor tableware includes a movable front end for carrying or picking up food. When the patient's hand is trembling, the front end will not be completely shaking, and the anti-tremor tableware can slow down the tremor of the patient's hand. However, it still cannot completely avoid spilling of the food.

SUMMARY OF CERTAIN INVENTIVE ASPECTS

For purposes of summarizing, certain aspects, advantages, and novel features have been described herein. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested herein.

In view of the above problems, in the actual test process of patients with hand tremors, the invention is continuously relined. The anti-tremor effect can be affected by the carrying portion held by the patient, the support portion for connecting to the tool or tableware, the connection between the anti-tremor module and the tool, and the design of the tool. Therefore, in light of the tested technology which can improve the anti-tremor effect, the present invention discloses an anti-tremor device, which can help to reduce the tool tremor and solve the problem that patients with hand tremor cannot eat on their own.

The anti-tremor device disclosed in one embodiment of the present invention includes a carrying portion that can be held by a user. For example, but not limited, the maximum outer diameter of the carrying portion is between 2 to 15 cm. Roughly, the carrying portion is made of a rigid material, which will not deform when the carrying portion is used or held by the user. For example, but not limited, the carrying portion is made of plastic. The carrying portion includes at least one opening and at least one support portion. The at least one opening allows the tool to pass through, and two ends or the periphery of the at least one support portion is disposed or mounted inside the carrying portion, including direct and indirect disposed or mounted inside the carrying portion. The support portion can support and mount the tool unit. The hard support portion that has at least two ends connecting to the carry portion, can also increase the strength of the carrying portion.

The anti-tremor device disclosed in an embodiment of the present invention includes a tool unit; the tool unit including a working end and a handle, and the working end is detachably mounted on a handle.

The anti-tremor device disclosed in an embodiment of the present invention includes a carrying portion and an anti-tremor module. The anti-tremor module is supported by the carrying portion. The anti-tremor module includes a frame body rotatable relative to the carrying portion, and at least one elastic body is provided between the frame body and the carrying portion or at the area of the rotation axis of the frame body, or a counterweight design is provided in the lower area of the frame body. One end of the elastic body is fixed to the frame body, and the other end of the elastic body is fixed to the carrying portion. The frame body has a connecting unit capable of fixing an additional tool, or the frame body and the connecting unit are connected through an elastic body.

Moreover, the end section of the tool unit can be bent downward, bolded, thickened, weighted, or the end section of the tool unit can include a counterweight structure that is integrally formed with the tool unit or movably mounted on the tool unit.

According to an embodiment of the present invention, a plurality of frame bodies in the carrying portion can be rotated relative to the carrying portion, and the smaller frame body is located in the larger frame body. At least one elastic body is fixed between two adjacent frame bodies, and the two adjacent frame bodies can be rotated relative to each other. The smaller frame has a connecting unit that can fix the additional tool, or the smaller frame and the connecting unit can be connected through an elastic body.

The anti-tremor device disclosed in an embodiment of the present invention includes a carrying portion having a pair of openings, a connecting unit, a groove or a clamp, a support portion which can connect the carrying portion with an additional unit, tableware, a container, a pen, a brush, a key, or a razor, or a middle section of the support portion, and a magnetic body can also be provided as the additional piece.

According to an embodiment of the present invention, at least one elastic body is fixed in the carrying portion. The periphery or two ends of the elastic body are fixed to the carrying portion. Include the different angles arrangement. A middle section of the elastic body can connect to a tool or an object directly, through a connecting unit, or through a jointing portion having an extension rod. The tool unit is movable or detachably connected to the jointing portion.

The middle section of the elastic body is a position where is between the two ends of the elastic body when the elastic body is a strip elastic body, or the middle section of the elastic body is the position where is not the periphery when the elastic body is a sheet elastic body.

According to an embodiment of the present invention, a connecting unit is provided in the middle section of the elastic body in the carrying portion, and the connecting unit can fix or remove the additional tools or tableware. The connecting unit can include at least one magnetic unit, at least one elastic unit, at least one clamping unit, at least one hole, at least one bearing, at least one tenon, at least one bump structure, at least one tube structure, at least one threaded structure, at least one columnar structure, at least one sawtooth structure, or a combination thereof.

According to an embodiment of the present invention, a plurality of elastic bodies are further fixed in the carrying portion, and the plurality of elastic bodies are arranged parallel to each other or have an angled arrangement including the case of connecting to each other or not. The periphery or the two ends of the elastic body are fixed to the carrying portion, and the middle section of the elastic body is connected to an area of the center of gravity of the tool by a protruding structure, chemical force, or mechanical force. The center of gravity of the tool unit can also be an area when the tool unit contains food in a normal condition, so that the center of gravity of the tool unit is a range.

The anti-tremor tool disclosed in an embodiment of the present invention includes a carrying portion. There is a counterweight or an asymmetric counterweight in the carrying portion. An elastic body is connected between the counterweight and the carrying portion, and the counterweight can slide relative to the carrying portion. Tableware can be fixed on the counterweight or the elastic body directly, through the connecting unit, or through the jointing portion. At least one bump or a plurality of bumps can be provided on the inner surface of the carrying portion. The jointing portion can include at least one magnetic unit, at least one elastic unit, at least one clamping unit, at least one hole, at least one bearing, at least one tenon, at least one bump structure, at least one tube structure, at least one threaded structure, at least one columnar structure, at least one sawtooth structure, or a combination thereof.

The anti-tremor device disclosed in another embodiment of the present invention includes a carrying portion, and an anti-tremor module is supported by or mounted in the carrying portion. The anti-tremor module includes a counterweight and a motor connected to each other. The motor can drive the counterweight to rotate relative to the carrying portion. The counterweight can connect to the carrying portion or the support portion in the carrying portion through a middle hole of a bearing, or the counterweight can connect to one end of a bearing, and the other end of the bearing is connected to the carrying portion or the support portion in the carrying portion. The carrying portion includes an assembly structure, a tenon, a hole, a magnetic body, or a bump structure, which can fix or remove the additional tools or tableware.

According to an embodiment of the present invention, a sensing circuit module is provided inside the carrying portion. The sensing circuit module includes a battery module, a sensing unit, an acceleration sensing unit, a processing unit, a control unit, an output unit, a memory component, a signal transmission component, a display component, or a touch component. The sensing circuit module can calculate the Fourier transform, can display the sensing data or result, can communicate signals with other devices, can measure, record, or analyze different axial vibrations, such as six-component of the axial vibrations, or can draw a polygonal diagram (for example: XYZ axis and XYZ axis rotation, the six-component hexagonal diagram).

According to an embodiment of the electronic anti-tremor module, the anti-tremor module may further include a charging component, so that the anti-tremor module can be charged more easily.

According to an embodiment of the present invention, a sensing circuit module can be provided inside an auxiliary holding portion.

The anti-tremor tool disclosed in an embodiment of the present invention includes a carrying portion and an auxiliary holding portion. The carrying portion or auxiliary holding portion may have decorations with patterns, glazing, broken diamond, diamond pattern, or acrylic. The auxiliary operation structure may include concave-convex structure, ring, opening, jointing portion, groove, fixture, concave-convex groove corresponding to human fingers, ergonomic structure, anti-slip material, rubber, silicone, thermoplastic material, devil felt belt, or length adjustable belt.

According to the anti-tremor tool and anti-tremor device disclosed by the present invention, a novel electronic anti-tremor module or a mechanical anti-tremor module is used to reduce or eliminate the vibration of the tool unit, with a stable tool unit, which helps people with tremor to eat on their own. The novel electronic anti-tremor module can also reduce the hand tremors of tremor patients. The novel anti-tremor module of the anti-tremor device disclosed by the present invention can have a better anti-tremor effect than the conventional anti-tremor device.

In some embodiments, a system can comprise, not comprise, consist essentially of, or consist of any number of features as disclosed herein.

In some embodiments, a method can comprise, not comprise, consist essentially of, or consist of any number of features as disclosed herein.

The details of one or more variations of the subject matter described herein are set forth in the accompanying drawings and the description below. Other features and advantages of the subject matter described herein will be apparent from the description and drawings, and from the claims. The disclosed subject matter is not, however, limited to any particular embodiment disclosed.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations as provided below.

The figures may not be to scale in absolute or comparative terms and are intended to be exemplary. The relative placement of features and elements may have been modified for the purpose of illustrative clarity. Where practical, the same or similar reference numbers denote the same or similar or equivalent structures, features, aspects, or elements, in accordance with one or more embodiments.

DETAILED DESCRIPTION OF CERTAIN ILLUSTRATIVE EMBODIMENTS

In the following, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

Figure 1A:
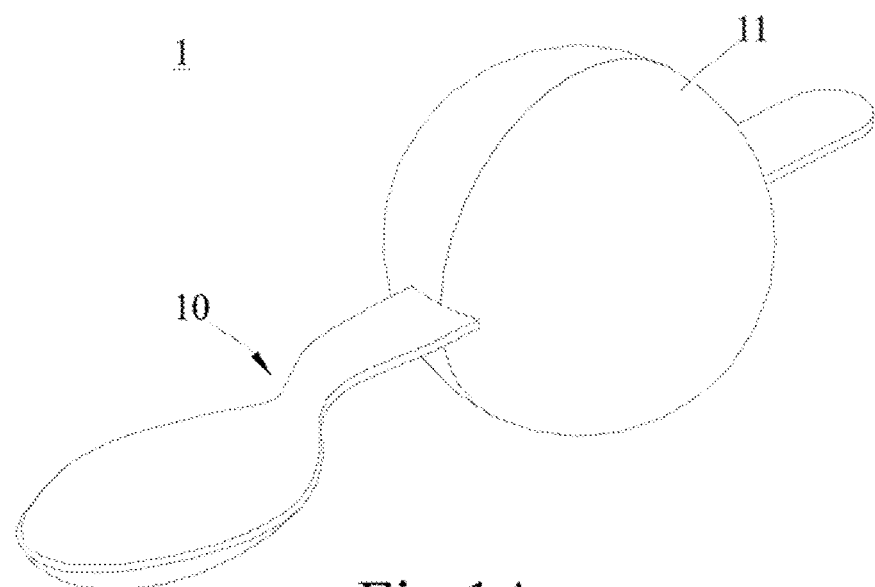
FIG. 1A is a schematic side view of an anti-tremor tool according to a first embodiment of the present invention.
Figure 1B:
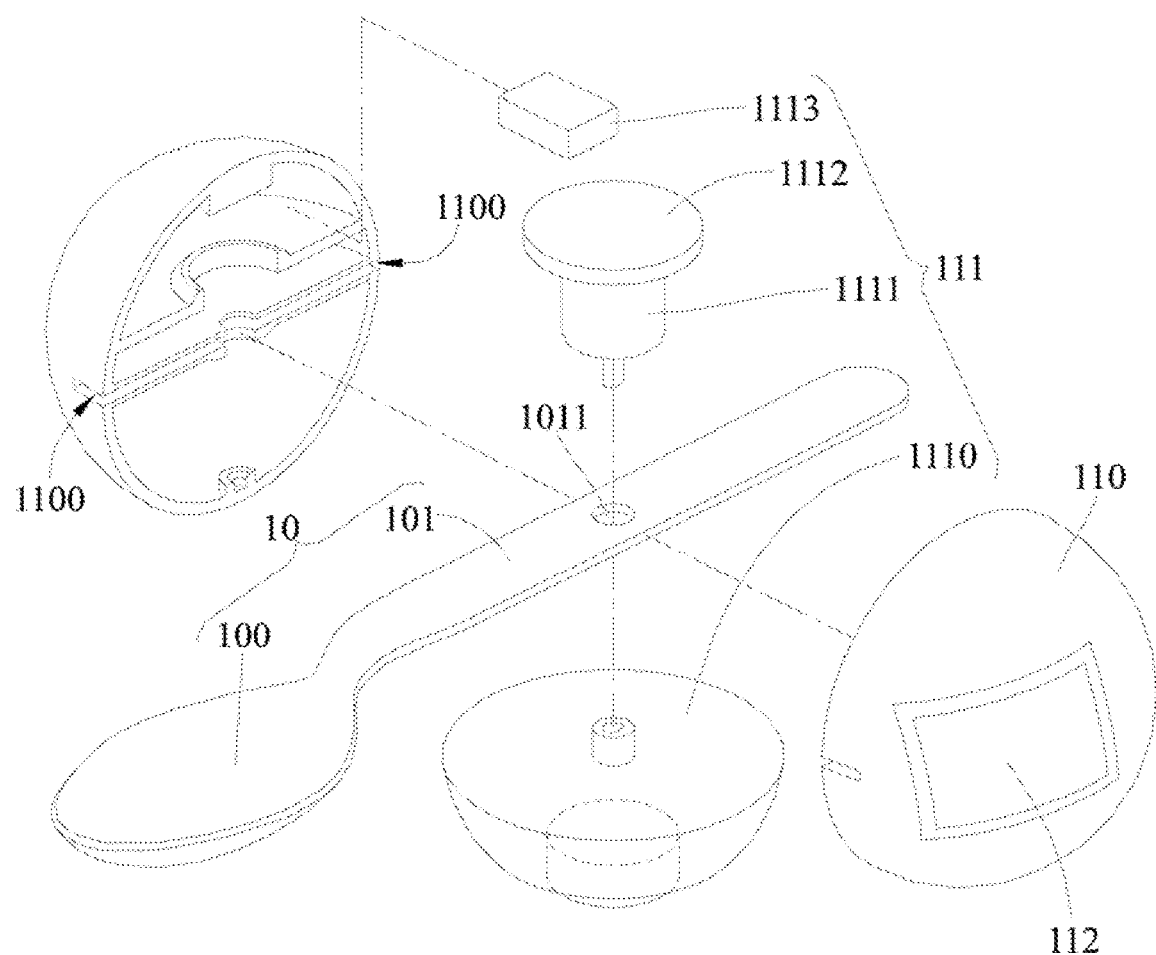
FIG. 1B is an exploded view of the anti-tremor tool of FIG. 1A.
Figure 1C:
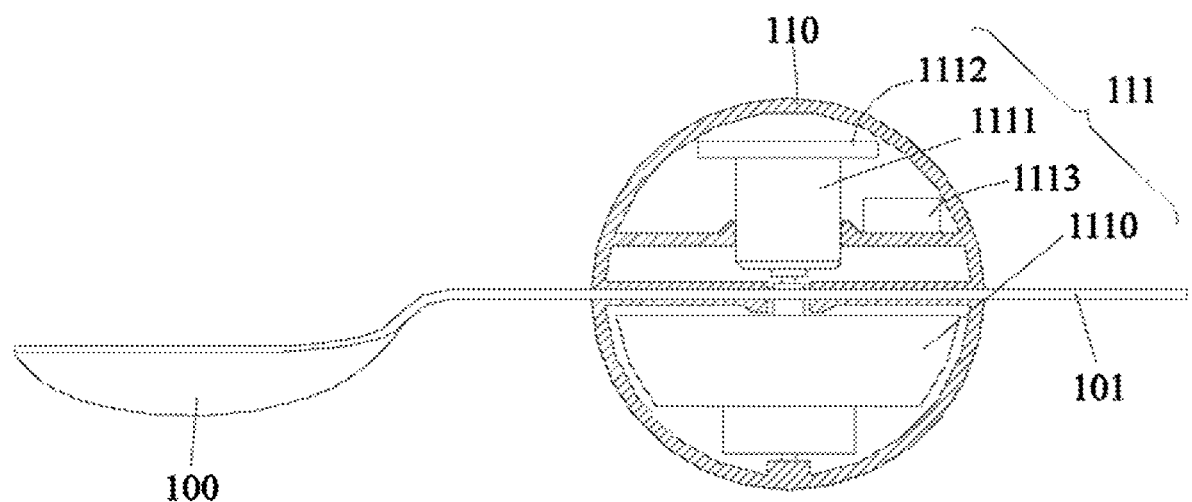
FIG. 1C is a schematic side sectional view of the anti-tremor tool of FIG. 1A.

Please refer to FIGS. 1A to 1C. FIG. 1A is a schematic side view of an anti-tremor tool according to a first embodiment of the present invention. FIG. 1B is an exploded view of the anti-tremor tool in FIG. 1A. FIG. 1C is a schematic side sectional view of the anti-tremor tool in FIG. 1A. In this embodiment, the anti-tremor tool 1 includes a tool unit 10 and an anti-tremor device 11.

In this embodiment, the tool unit 10 is a spoon, and its working end portion 100 can carry liquid or solid food. The tool unit 10 includes a working end portion 100 and a handle portion 101 connected to each other. Further, the working end portion 100 and the handle portion 101 may be detachably connected to each other In other embodiments, the tool unit may be other assistant objects, such as forks, knives, chopsticks, and other tableware, or other daily objects, such as containers, pens, brushes, keys, razors, toothbrush.

The anti-tremor device 11 includes a carrying portion 110 and an anti-tremor module 111. The carrying portion 110 is, for example, but not limited to a spherical plastic case, and is disposed or mounted on the handle portion 101 of the tool unit 10. In detail, two opposite sides of the carrying portion 110 are respectively provided with two openings 1100, and the handle portion 101 of the tool unit 10 is inserted through the two openings 1100. Furthermore, the openings 1100 can each be a groove.

The anti-tremor module 111 is mounted in the carrying portion 110. The anti-tremor module 111 includes a counterweight 1110, a motor 1111, a control module 1112, and a power source 1113. The counterweight 1110 is, for example, but not limited to, a metal disk, which is disposed on a rotating shaft connected to the motor 1111 to adjust the inertia of the anti-tremor module 111.

Figure 1D:
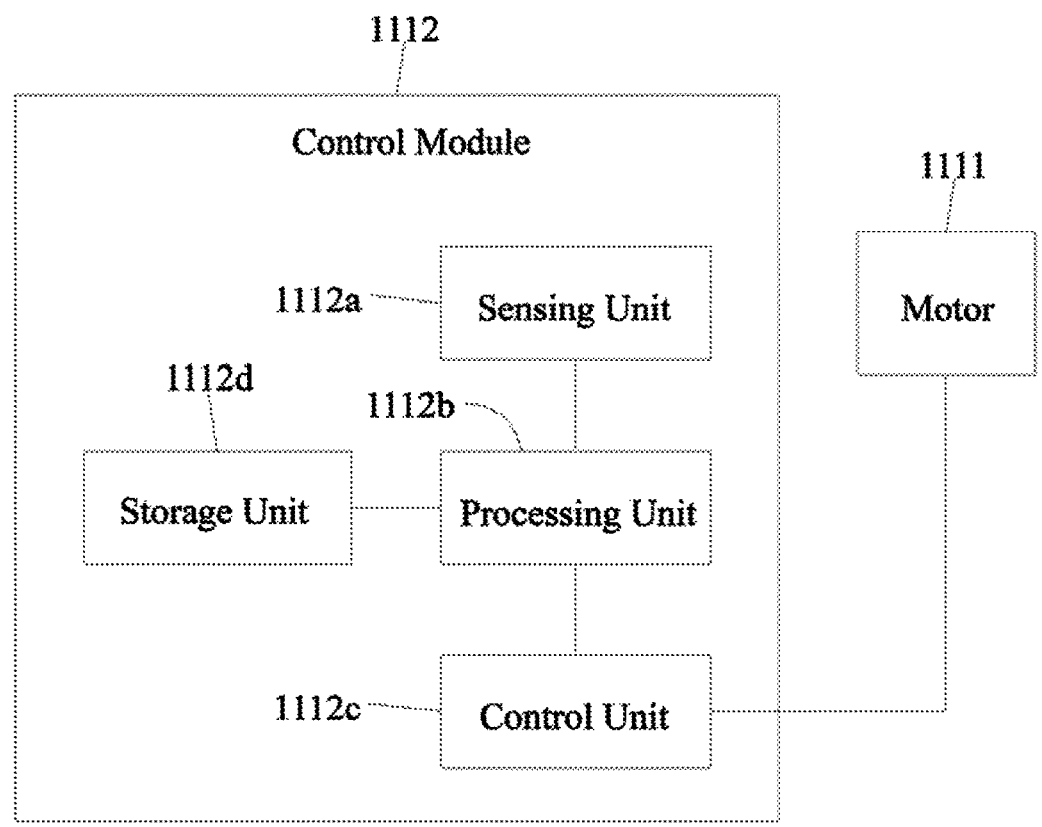
FIG. 1D is a block diagram of a control module of the anti-tremor tool of FIG. 1A.
Figure 1E:
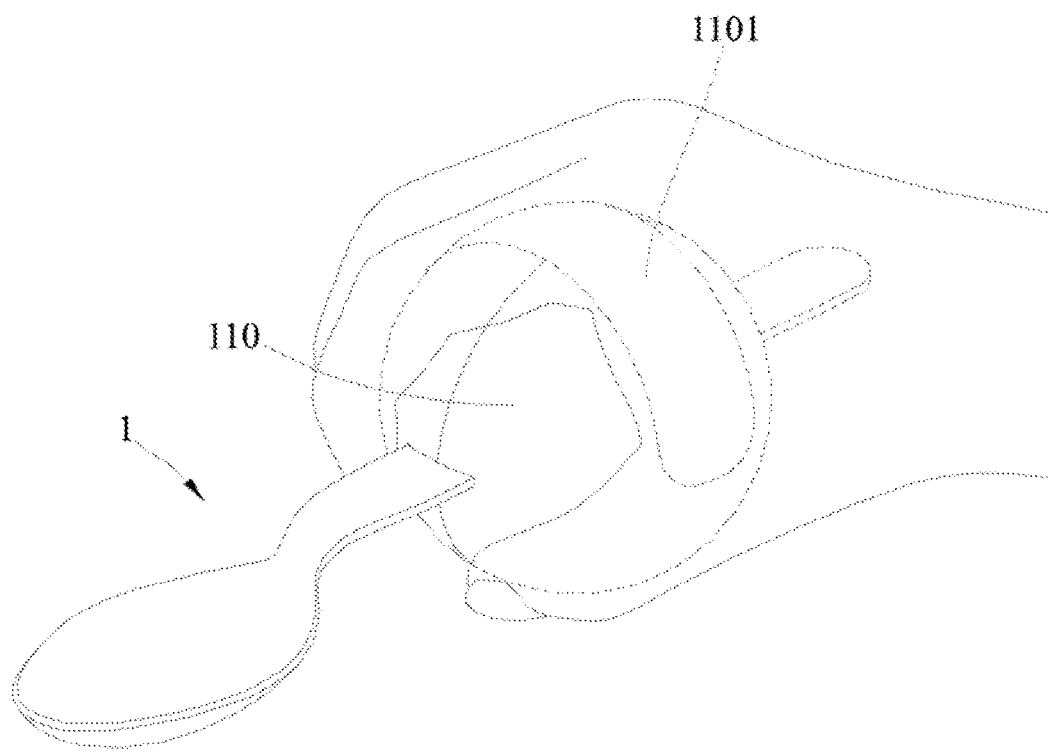
FIG. 1E is a schematic perspective view of a user holding the anti-tremor tool of FIG. 1A.

The rotating shaft connected to the motor 1111 passes through the hole 1011 of the handle portion 101 of the tool unit 10. FIG. 1D is a block diagram of a control module of the anti-tremor tool of FIG. 1A. The control module 1112 mounted in the carrying portion 110 and includes a sensing unit 1112a, a processing unit 1112b, and a control unit 1112c. The sensing unit 1112a, the processing unit 1112b, and the control unit 1112c are all mounted on the inner wall of the carrying portion 110. The sensing unit 1112a is, for example, a tremor sensing unit. The processing unit 1112b has an arithmetic logic function, and is coupled to the sensing unit 1112a. The control unit 1112c is coupled to the processing unit 1112b and the motor 1111. The functions of the sensing unit 1112a, the processing unit 1112b, and the control unit 1112c will be further described below.

The power source 1113 is electrically connected to the motor 1111 and the control module 1112. The power source 1113 can provide power to the motor 1111, to drive the motor 1111 to drive the counterweight 1110 to rotate relative to the carrying portion 110.

Moreover, in other embodiment, the carrying portion 110 includes a tool unit assembly structure, which can detachably install the tool unit 10. The tool unit assembly structure can be a tenon, a hole, a magnetic body, or a bump structure.

The user can grasp the carrying portion 110 to hold the anti-tremor tool 1. In addition, a non-slip structure or material 1101 can be provided on the outer surface of the carrying portion 110, and the area of the non-slip structure or material 1101 is less than or equal to the total area of the carrying portion 110. When the user holds the carrying portion 110, the hand can contact the non-slip structure 1101. When the carrying portion 110 vibrates due to the user's hand tremor, the sensing unit 1112a of the anti-tremor module 111 detects the tremor and generates a tremor signal. The tremor signal is transmitted by the sensing unit 1112a to the processing unit 1112b and received by the processing unit 1112b. The processing unit 11126 generates a feedback signal for changing the rotation speed of the motor 1111 according to the received tremor signal. In detail, the arithmetic logic function of the processing unit 1112b can analyze the tremor signal to confirm the tremor degree of the carrying portion 110 (that is, the displacement or acceleration of the carrying portion 110 moving back and forth), and then generate a feedback signal according to the degree of tremor. The feedback signal is received by the control unit 1112c. The control unit 1112c generates a control signal according to the received feedback signal and transmits the control signal to the motor 1111 to change the rotation speed.

The sensing unit 1112a and the processing unit 1112b sense the strength of the tremor of the carrying portion 110, and then cause the control unit 1112c to accelerate or decelerate the motor 1111 by increasing or decreasing the current provided to the motor 1111. When the rotation speed of the motor 1111 changes, the rotation speed of the counterweight 1110 connected to the motor 1111 also changes, so that the moment of inertia of the counterweight 1110 increases or decreases according to the rotation speed of the counterweight 1110. When the inertia of the counterweight 1110 increases, the effect for reducing or eliminating the tremor of the carrying portion 110 at the same time, the user's hand tremors can be decreased, thereby achieving the anti-tremor effect. Therefore, patients with body tremor can use the anti-tremor tool 1 to eat on their own.

In this embodiment, when the user picks up the anti-tremor tool 1, the sensing unit can detect that the carrying portion is changed from static to moving, and the processing unit will turn on the motor current. This is an auto switch to turn on the anti-tremor tool 1.

Furthermore, in other embodiments, the anti-tremor module 111 may include a wireless transmission unit to connect to an outer electronic device, such as a mobile phone or a computer, or may include a display 112, and the control module 1112 may further include a storage unit 1112d. The storage unit 1112d is coupled to the processing unit 1112b. When the user's hand tremor increases or decreases, the sensing unit 1112a generates a sensing signal according to the increase or decrease of the tremor degree of the carrying portion 110. The sensing signal is processed into data by the processing unit 1112b and can be displayed on the display 112, so that the user can view related medical information.

In another embodiment, the carrying portion 110 further includes an assembly structure, a tenon, a hole, a magnetic body, or a bump structure for fixing or detaching an additional working end portion of the tool unit or the tableware.

Figure 2:
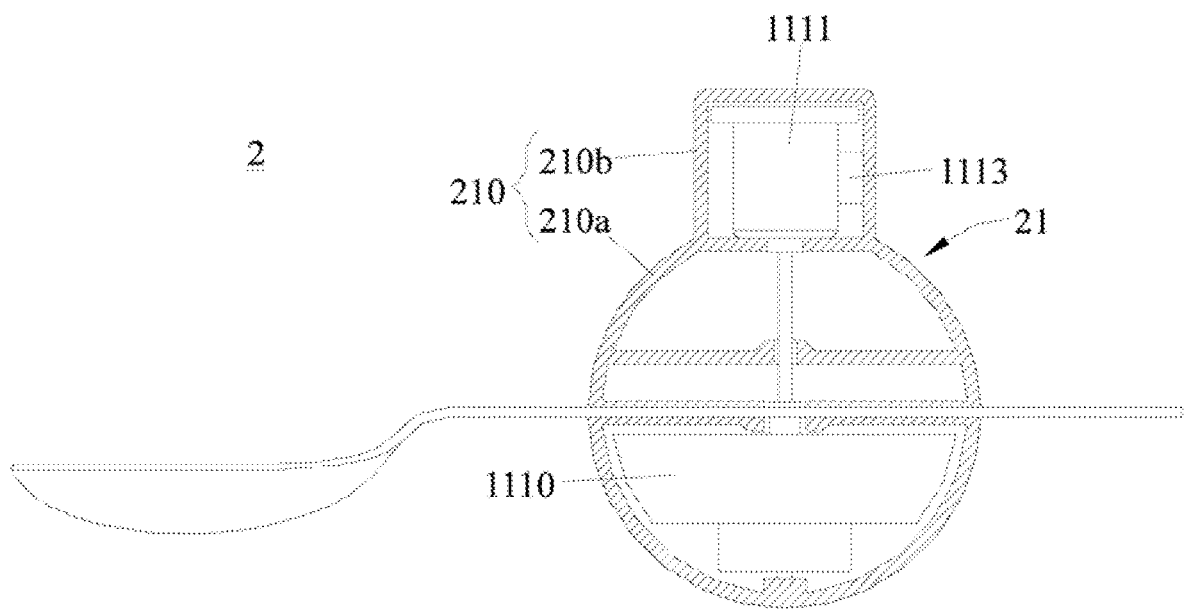
FIG. 2 is a schematic side sectional view of an anti-tremor tool according to a second embodiment of the present invention.

FIG. 2 is a schematic side sectional view of an anti-tremor tool according to a second embodiment of the present invention. Since this embodiment is similar to the first embodiment, and only the differences between the first embodiment and the second embodiment will be described below.

In this embodiment, the carrying portion 210 of the anti-tremor device 21 of the anti-tremor tool 2 includes a main case 210a and a sub-case 210b detachably mounted on the main case 210a. The main case 210a and the sub-case 210b can be assembled closely, or elastic material is sandwiched between the main case 210a and the sub-case 210b to fill a gap that may exist between the main case 210a and the sub-case 210b. The counterweight 1110 of the anti-tremor module 111 is supported by the main case 210a, and the motor 1111 and the power source 1113 are mounted in the sub-case 210b. Therefore, when the anti-tremor tool 2 needs to be cleaned, the sub-case 210b can be detached to prevent the motor 1111 and the power source 1113 from getting wet. The counterweight can be mounted in the main case 210a, and one of or both of the motor and the battery are mounted in the sub-case 210b.

Figure 3:
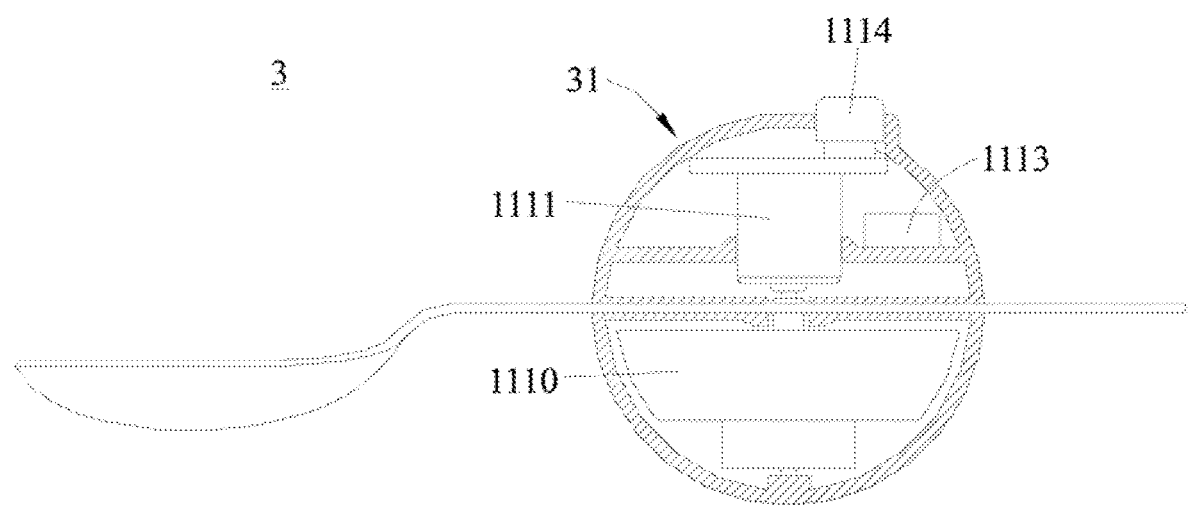
FIG. 3 is a schematic side sectional view of an anti-tremor tool according to a third embodiment of the present invention.

FIG. 3 is a schematic side sectional view of an anti-tremor tool according to a third embodiment of the present invention. Since this embodiment is similar to the first embodiment, only the differences between the first embodiment and the third embodiment will be described below.

In this embodiment, the anti-tremor device 31 of the anti-tremor tool 3 does not have the control module, but includes a counterweight 1110, a motor 1111, a power source 1113, and a power switch 1114. The power source 1113 is electrically connected to the motor 1111, and the power switch 1114 is used to turn on or off the electrical connection between the power source 1113 and the motor 1111. Therefore, the user can turn on or off the anti-tremor function of the anti-tremor tool by the power switch 1114. In other embodiment, such a power switch 1114 can also mounted in the above embodiment which has power, to control the power on or off.

Figure 4A:
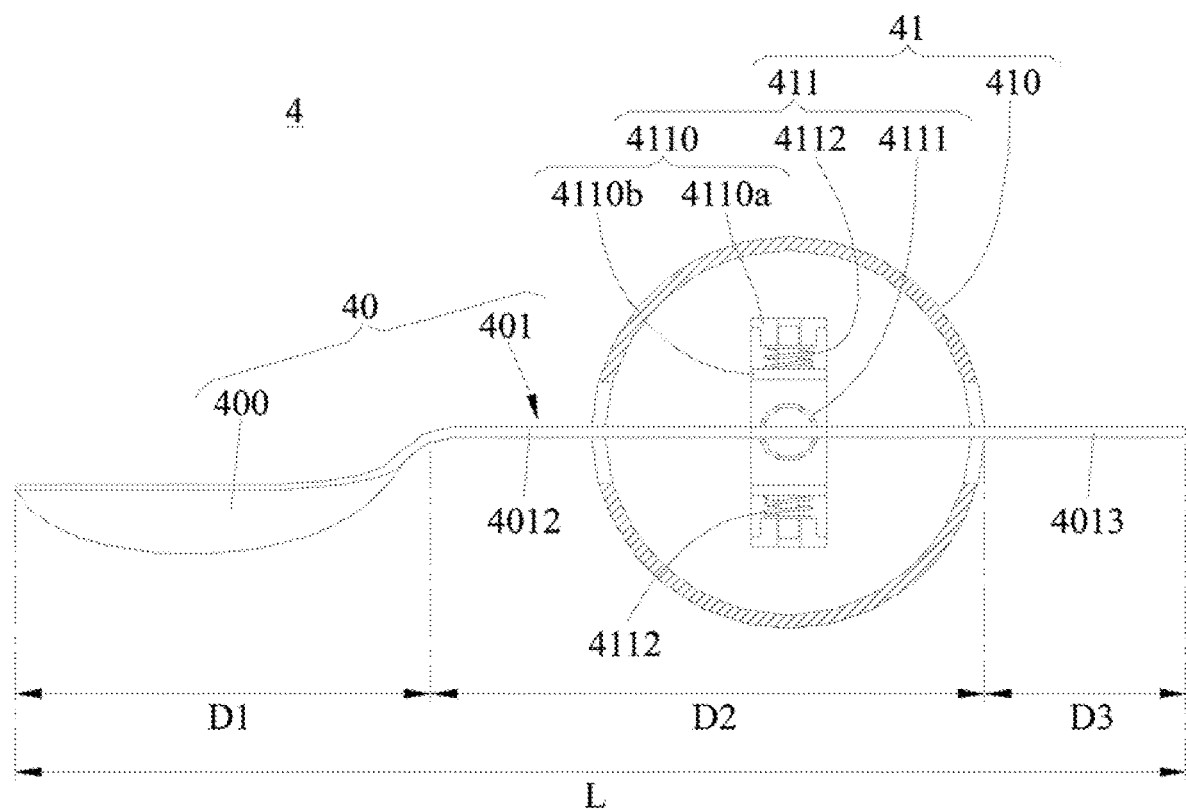
FIG. 4A is a schematic side sectional view of an anti-tremor tool according to a fourth embodiment of the present invention.
Figure 4B:
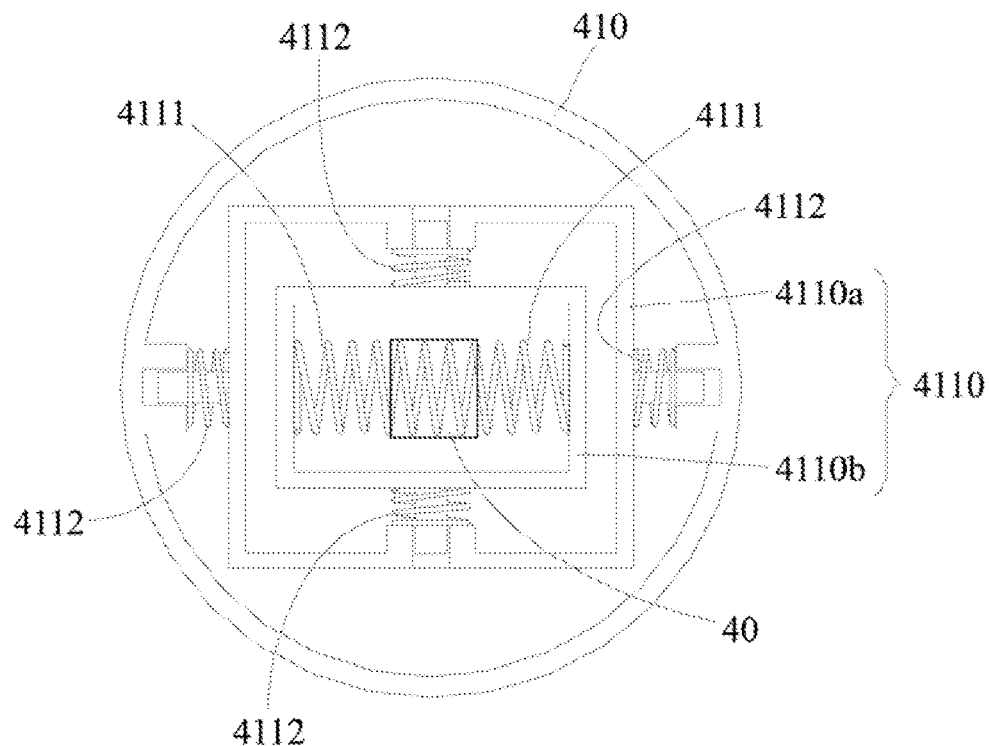
FIG. 4B is a side cutaway schematic view of the internal perspective of the anti-tremor tool of FIG. 4A.

In addition to the electronic anti-tremor device of the first embodiment, the present invention also discloses a mechanical anti-tremor device. Please refer to FIGS. 4A and 4B. FIG. 4A is a schematic side sectional view of an anti-tremor tool according to a fourth embodiment of the present invention. FIG. 4B is a side cutaway schematic view of the internal perspective of the anti-tremor tool of FIG. 4A. In this embodiment, the anti-tremor tool 4 includes a tool unit 40 and an anti-tremor device 41, and the anti-tremor device 41 includes a carrying portion 410, and an anti-tremor module 411.

The tool part 40 includes a working end and a handle, and can be integrally formed. In another case where the working end of the tool is detachably connected to the handle; the detachable working end portion can be a spoon, a fork, or other required tools.

The carrying portion 410 includes a holding portion, which will not deform when in use; The carrying portion 410 has at least one opening, so that the tool can pass through; An anti-tremor module or at least one support portion is mounted in the carrying portion 410, and two ends or the periphery of the support portion is connected to the carrying portion 410.

The anti-tremor module 411 is mounted in the carrying portion 410 and includes a frame body portion 4110 and an elastic body 4111. The frame body portion 4110 is movably mounted in the carrying portion 410. In detail, the frame body portion 4110 includes a first frame body 4110a and a second frame body 4110b having different sizes. The larger first frame body 4110a is pivotally mounted in the carrying portion 410. The smaller second frame body 4110b is pivotally mounted in the first frame body 4110a, and the first frame body 4110a surrounds the second frame body 4110b. An elastic body 4111 is mounted on the second frame body 4110b of the frame body portion 4110. A tool unit assembly structure is formed between the elastic body 4111 and the tool unit 40, the tool unit 40 is supported by the elastic body 4111. The number of elastic bodies 4111 is not intended to limit the invention. Moreover, the elastic body 4112 can also replace the shaft inside, and the shaft is disposed between the frame body portion 4110 and the carrying portion 410.

The conventional anti-tremor device cannot completely solve the problem of tremor of the tool unit caused by human tremor. One reason is that the conventional anti-tremor device can only achieve the anti-tremor effect in one of the vertical and horizontal directions. In order to overcome the shortcomings of the conventional anti-tremor device, the anti-tremor module 411 of this embodiment includes a frame 4110 pivotally mounted on the carrying portion 410. As the frame portion 4110 can be rotatable or moved relative to the carrying portion 410, and also the elastic body 4111 can effectively reduce or eliminate the tremor of the carrying portion 410 in various directions (including both vertical and horizontal directions).

In addition, most of the conventional anti-tremor tools with anti-tremor function have an anti-tremor device at the end of the tool unit. When the user holds the anti-tremor device, this kind of anti-tremor device will reduce the anti-tremor function. In order to solve the above problems, in this embodiment, the carrying portion 410 and the anti-tremor module 411 are mounted at the middle section of the tool unit 40. In detail, the handle portion 401 of the tool unit 40 includes an extension section 4012 and an end section 4013 connected to each other. The extension section 4012 is interposed between the working end 400 and the end section 4013. Both the carrying portion 410 and the anti-tremor module 411 are disposed or mounted on the extension section 4012. Furthermore, the sum of the length D1 of the working end portion 400, the length D2 of the extension section 4012, and the length D3 of the end section 4013 is equal to the overall length L of the tool unit 40, and the length D2 of the extension section 4012 is less than or equal to half of the overall length L. In this way, when the user holds the carrying portion 410 of the anti-tremor device 41, the elastic body 4111 of the anti-tremor module 411 can prevent the deformation and affect the anti-tremor effect because of the weight of the tool unit 40. In another embodiment, the tool unit 40 can only include the working end portion 400.

In addition, the frame body 4110 of this embodiment further includes a plurality of elastic bodies 4112. These elastic bodies 4112 are respectively disposed at the pivots between the first frame body 4110a and the carrying portion 410, and the pivots of any two adjacent frame bodies, such as the first frame body 4110a and the second frame body 4110b, thereby helping to make the anti-tremor module 411 achieve a better anti-tremor effect.

In this embodiment, the frame portion 4110 includes two frame bodies, but the present invention is not limited thereto. In other embodiments, the frame body portion is a single frame body, or the frame body portion includes three or more frame bodies of different sizes, and the elastic body is mounted on the frame of the smallest size. In addition, the first frame body 4110a of this embodiment is pivotally mounted in the carrying portion 410, and the second frame body 4110b is pivotally mounted in the first frame body 4110a, but this connection method is not intended to limit the present invention. In other embodiments, the first frame body and the carrying portion may be connected to each other with a spring or a torsion spring, and the first frame body and the second frame body may also be connected to each other with a spring or a torsion spring.

Figure 5:
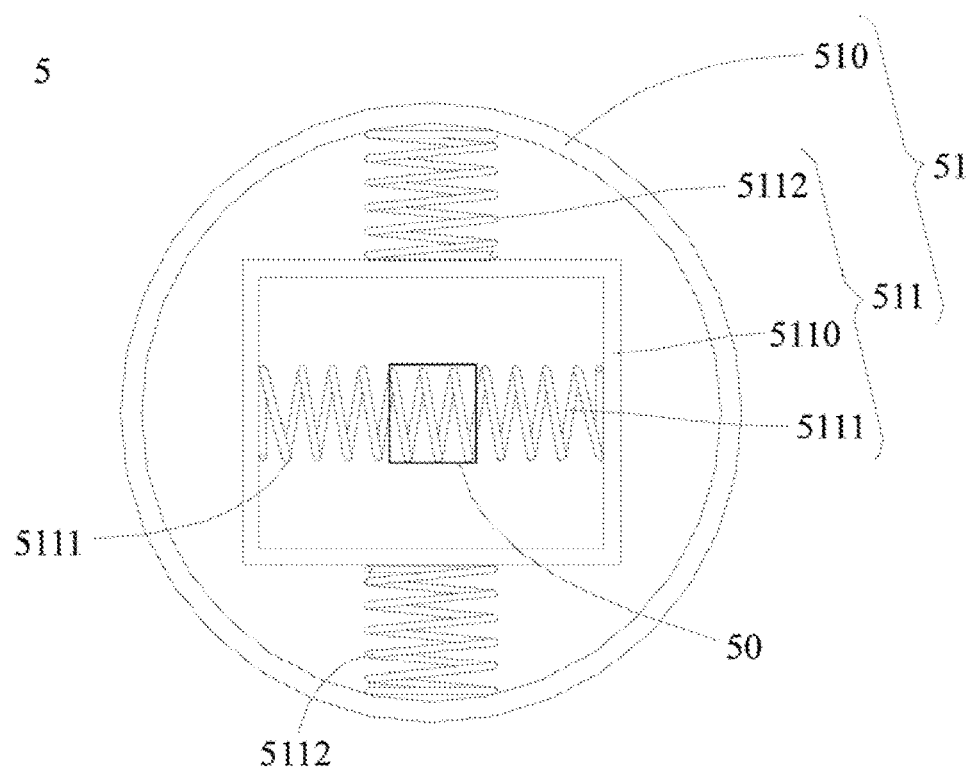
FIG. 5 is a schematic side sectional view of the inside of an anti-tremor tool according to a fifth embodiment of the present invention.

FIG. 5 is a schematic side sectional view of the inside of an anti-tremor tool according to a fifth embodiment of the present invention. Since the fifth embodiment is similar to the fourth embodiment, the differences between the fifth embodiment and the fourth embodiment will be described below.

In this embodiment, the anti-tremor tool 5 includes a tool unit 50 and an anti-tremor device module 51, and the anti-tremor device module 51 includes a carrying portion 510 and an anti-tremor module 511. For example, the carrying portion 510 is a frame body, which can connect to an auxiliary holding portion or mount in the auxiliary holding portion. The tool unit 50 and the carrying portion 510 are described in detail in the fourth embodiment, which will not be described in detail below.

The anti-tremor module 511 is mounted in the carrying portion 510 and includes a frame body 5110, a first elastic body 5111, and two second elastic bodies 5112. Two ends of the first elastic body 5111 are mounted on the left side and the right side of the frame 5110. A tool unit assembly structure is termed between the first elastic body 5111 in the frame body 5110 and the tool unit 50, and the tool unit 50 is supported by the elastic body 5111. The two second elastic bodies 5112 are respectively mounted on the upper side and the lower side of the frame 5110, so that the frame 5110 is mounted on the carrying portion 510 via the second elastic bodies 5112, and the deformation direction of the second elastic body 5112 is substantially orthogonal to the deformation direction of the first elastic body 5111. The number of the first elastic body 5111 and the second elastic body 5112 is not intended to limit the present invention.

In this embodiment, the deformation direction of the second elastic body 5112 is substantially orthogonal to the deformation direction of the first elastic body 5111, but the present invention is not limited thereto. In other embodiments, the deformation direction of the second elastic body 5112 intersects with the deformation direction of the first elastic body 5111, for example, an acute angle is formed between the extension lines of the deformation directions of the first elastic body and the second elastic body.

Figure 6:
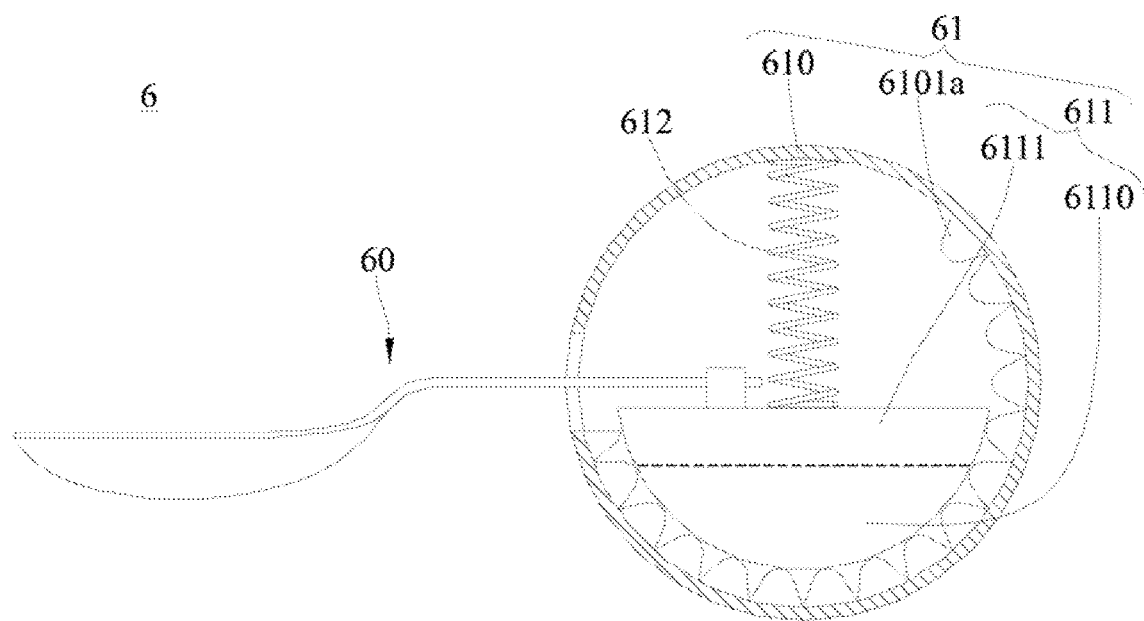
FIG. 6 is a schematic side sectional view of an anti-tremor tool according to a sixth embodiment of the present invention.

FIG. 6 is a schematic side sectional view of an anti-tremor tool according to a sixth embodiment of the present invention. In this embodiment, the anti-tremor tool 6 includes a tool unit 60 and an anti-tremor device 61, and the anti-tremor device 61 includes a carrying portion 610 and a counterweight 611, and the elastic body 612 connected the carrying portion 610 and the counterweight 611.

The inner surface of the carrying portion 610 has a bump structure 6101a. The counterweight 611 is mounted in the carrying portion 610, and the counterweight 611 is in contact with the bump structure 6101a. The bump structure 6101a helps to reduce the friction between the inner surface of the carrying portion 610 and the counterweight 611, so that the counterweight 611 can be smoothly moved relative to the carrying portion 610 while being supported by the bump structure 6101a, which helps to reduce or eliminate the tremor of the carrying portion 610. An elastic body 612 is connected between the counterweight 611 and the carrying portion 610, and the counterweight 611 can slide relative to the carrying portion 610. The tool unit 60 can be supported by the counterweight 611 or by the elastic body 612. The tool unit 60 can also connect to the counterweight 611 or the elastic body 612 through a tool unit assembly structure.

The counterweight 611 includes a load portion 6110 and a carrying portion 6111 located on one side of the load portion 6110. The tool unit 60 is provided on the carrying portion 6111. The load portion 6110 is farther from the tool unit 60 than the load portion 6111, The counterweight 611 can reduce the sensitivity of tool unit 60 to tremor, so as to reduce or eliminate the tremor transfer to the tool unit 60.

The counterweight 611 in this embodiment is a load with uneven weight distribution, but it is not limited thereto. In other embodiments, the weight distribution of the weight 611 may be uniform. The weight distribution is adjusted, for example, to add an additional counterweight or to make the shape of the weight 611 symmetrical or asymmetrical.

Figure 7A:
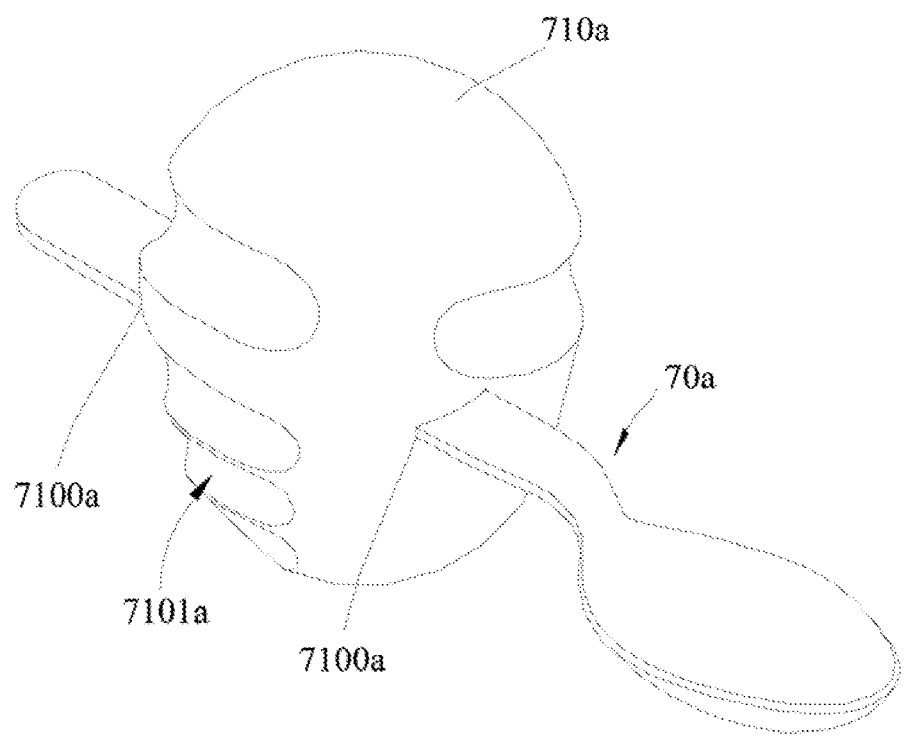
FIG. 7A is a schematic side view of an anti-tremor tool according to a seventh embodiment of the present invention.

FIG. 7A is a schematic side view of an anti-tremor tool according to a seventh embodiment of the present invention. The anti-tremor tool 7a includes a carrying portion 710a and a tool unit 70a. The carrying portion 710a is mounted on an extension section of a handle portion of the tool unit 70a, and a front end and a rear end of the tool unit 70a are respectively inserted throughout two openings 7100a of the carrying portion 710a. An auxiliary operation structure 7101a is provided on the outer surface of the carrying portion 710a. The shape of the auxiliary operation structure 7101a matches the posture of the hand and the position of the fingers when the user holds the carrying portion 710a. In this way, when the user uses the anti-tremor tool 7a, the hand can be placed in the same position, which can prevent the anti-tremor effect from being affected by the user's improper holding posture and make the carrying portion easily to hold.

Figure 7B:
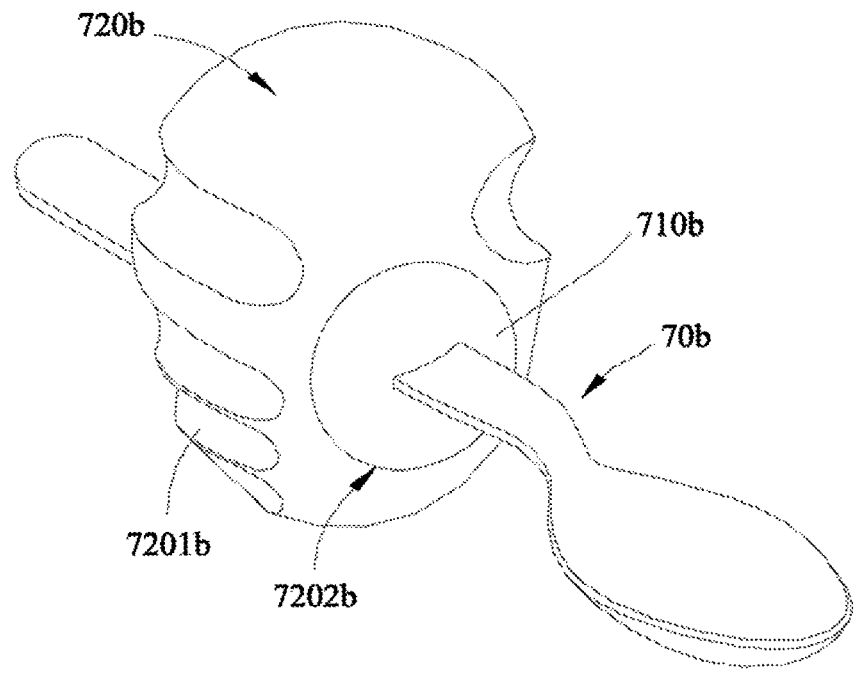
FIG. 7B is another schematic side view of an anti-tremor tool according to the seventh embodiment of the present invention.

FIG. 7B is another embodiment, shows schematic side view of the anti-tremor tool similar to the seventh embodiment of the present invention. The anti-tremor tool 7b further includes an auxiliary holding portion 720b, and an auxiliary operation structure 7201b is provided on an outer surface of the auxiliary holding portion 720b. The auxiliary holding portion 720b has an assembly structure 7202b, such as a groove but it is not limited thereto. The carrying portion 710b can be inserted into the auxiliary holding portion 720b through the assembly structure 7202b, and the auxiliary holding portion 720b can be detachably mounted on the carrying portion 710b, so that the user can install or detach the auxiliary holding portion 720b at any time as needed.

In other embodiments, the auxiliary holding portion can be moved or rotated relative to the carrying portion and the surface or an outer side of the auxiliary holding portion has the appearance design similar to the carrying portion.

Figure 8:
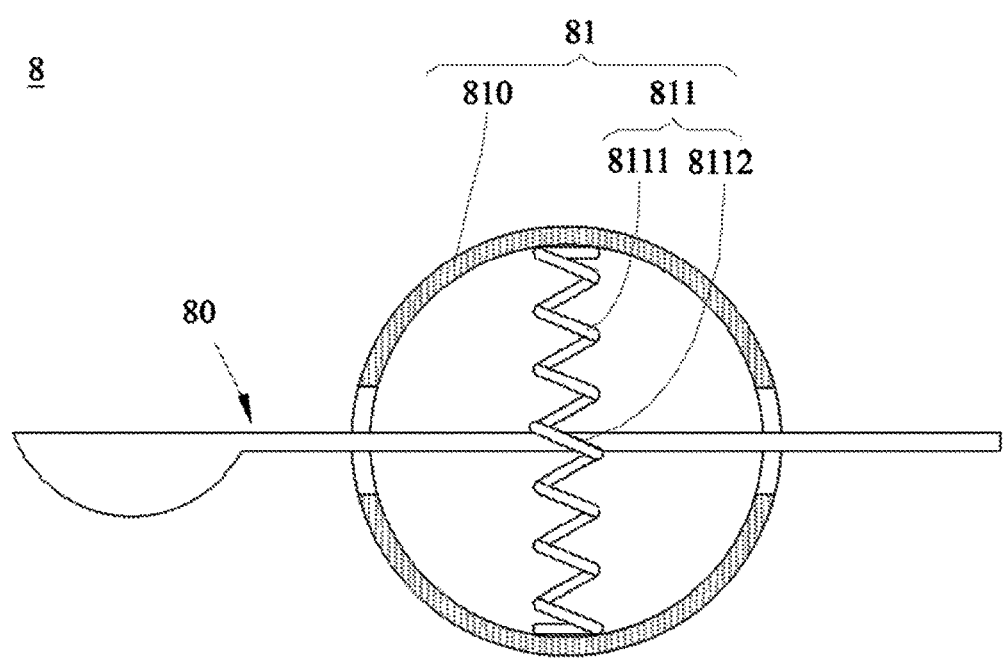
FIG. 8 is a schematic side sectional view of an anti-tremor tool according to an eighth embodiment of the present invention.

FIG. 8 is a schematic side sectional view of an anti-tremor tool according to an eighth embodiment of the present invention. In this embodiment, the anti-tremor tool 8 includes a tool unit 80 and an anti-tremor device 81, and the anti-tremor device 81 includes a carrying portion 810 and an anti-tremor module 811. The tool unit 80 and the carrying portion 810 are described in detail in the fourth embodiment, which will not be described below. The anti-tremor module 811 includes an elastic body 8111, and two ends of the elastic body 8111 are mounted in the carrying portion 810, and the elastic body 8111 has a tool unit assembly structure 8112. The tool unit 80 is supported by the anti-tremor module 811 through the tool unit assembly structure 8112. The tool unit assembly structure 8112 is, for example but not limited to, a tenon mechanism or a concave-convex structure.

In addition, the tool unit 80 may be exactly mounted in or connected to the middle of the elastic body 8111, that is, the distance between the opposite ends of the elastic body 8111 and the tool unit 80 is substantially equal. In another embodiment, the position of the tool unit 80 mounted in the elastic body 8111 may be biased toward one end of the elastic body 8111, that is, the distance between the tool unit 80 and the end of the elastic body 8111 near the top of the load carrying portion 810 is smaller than the distance between the tool unit 80 and the end of the elastic body 8111 near the bottom of the load carrying portion 810. In other embodiments, an area of a center of gravity of the tool unit 80 can be directly mounted in or support by the elastic body 8111.

Figure 9A:
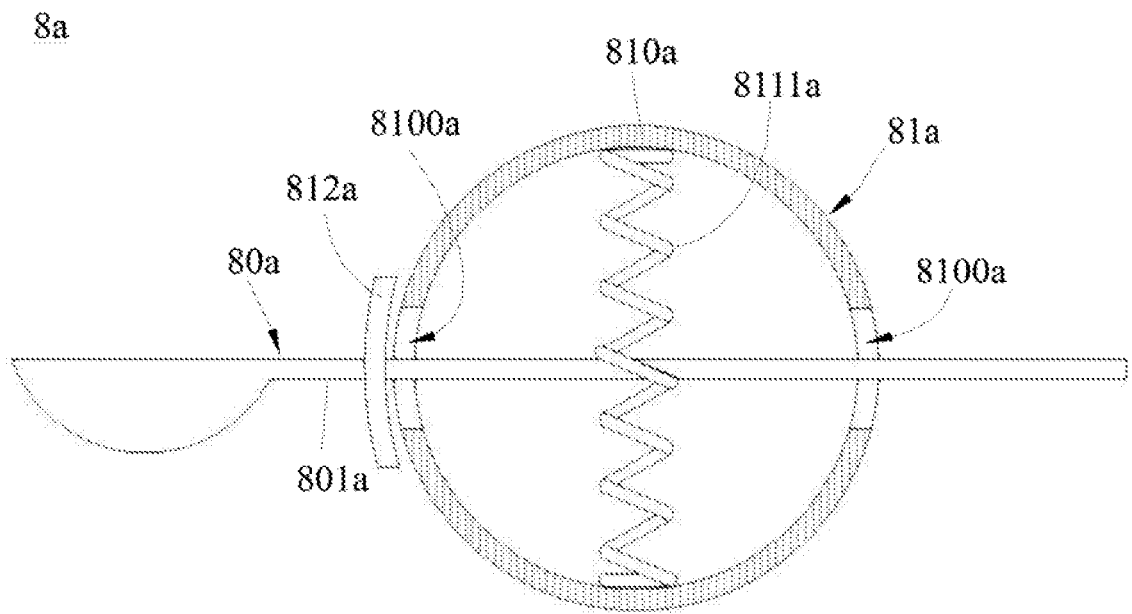
FIG. 9A is a schematic side sectional view of an anti-tremor tool according to a ninth embodiment of the present invention.

FIG. 9A is a schematic side sectional view of an anti-tremor tool according to a ninth embodiment of the present invention. The ninth embodiment is similar to the eighth embodiment, and the differences between the ninth embodiment and the eighth embodiment will be described below.

The tool unit 80a of the anti-tremor tool 8a is directly connected to or mounted on a middle section of the elastic body 8111a, and there is no tool unit assembly structure or jointing portion. The anti-tremor tool 8a further includes a baffle 812a. The baffle 812a is disposed of adjacent to the opening 8100a of the carrying portion 810a. The baffle 412 is not connected to the opening 8100a, and the baffle 412 is larger than the opening 8100a. The baffle 412 may have a flat or curved shape.

Figure 9B:
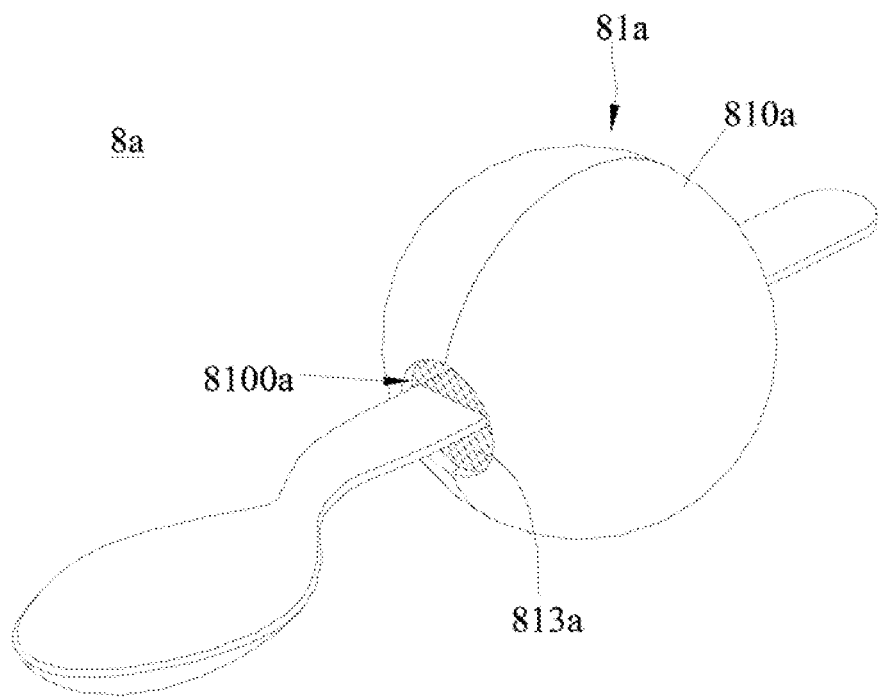
FIG. 9B is a schematic side view of the anti-tremor tool according to the ninth embodiment of the present invention.

FIG. 9B is another schematic side view of an anti-tremor tool according to the ninth embodiment of the present invention. Taking the anti-tremor tool 8a of the ninth embodiment as an example, the anti-tremor tool 8a further includes a waterproof and dustproof film 813a. The waterproof and dustproof film 813a is disposed on the opening 8100a of the carrying portion 810a of the anti-tremor device 81a. The baffle 812a and the waterproof and dustproof film 813a help to prevent objects from moving from the opening 8100a into the carrying portion 810 when the user uses the anti-tremor tool 8a. FIG. 9A and FIG. 9B show that a baffle 812a or a waterproof and dustproof film 813a is provided near one of the two openings 8100a of the carrying portion 810a, but the invention is not limited thereto. In other embodiments, a baffle 812a or a waterproof and dustproof film 813a is provided near the two pairs of openings 8100a opposite to the carrying portion 810a. In another embodiment, the waterproof and dustproof film 813a can be replaced by an elastic film.

Figure 10:
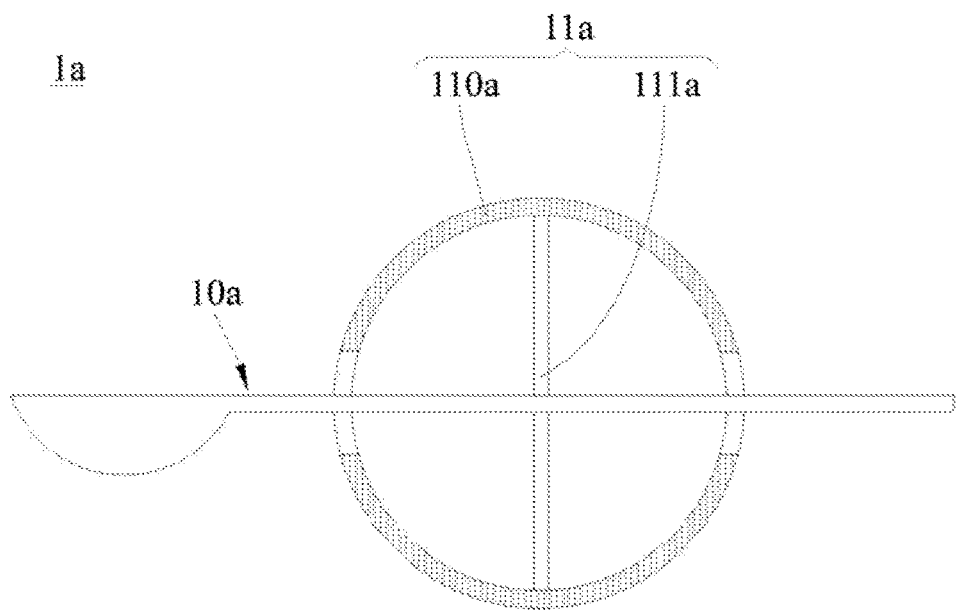
FIG. 10 is a schematic side sectional view of an anti-tremor tool according to a tenth embodiment of the present invention.

FIG. 10 is a schematic side sectional view of an anti-tremor tool according to a tenth embodiment of the present invention. In this embodiment, the anti-tremor tool 1a includes a tool unit 10a and an anti-tremor device 11a. The anti-tremor device 11a includes a carrying portion 110a and an anti-tremor module 111a. The tool unit 10a and the carrying portion 110a are described in detail in the fourth embodiment, which will not be described in detail below. Two ends of a support portion 111a are connected to the carrying portion 110a, and the support portion 111a may be a non-elastic rod or an elastic body. The tool unit 10a may be inserted through the carrying portion 111a, or may be mounted on the tool unit assembly structure formed between two ends of the support portion 111a. For example but not limited thereto, the tool unit assembly structure may be a hole or a bearing. The tool unit 10a may be inserted through the tool unit assembly structure to be mounted on the support portion 111a. In other embodiments, the support portion 111a may be replaced by an elastic body. Further, the tool unit 10a is fixedly or detachably connected to the anti-tremor module 111a through the tool unit assembly structure.

Figure 11:
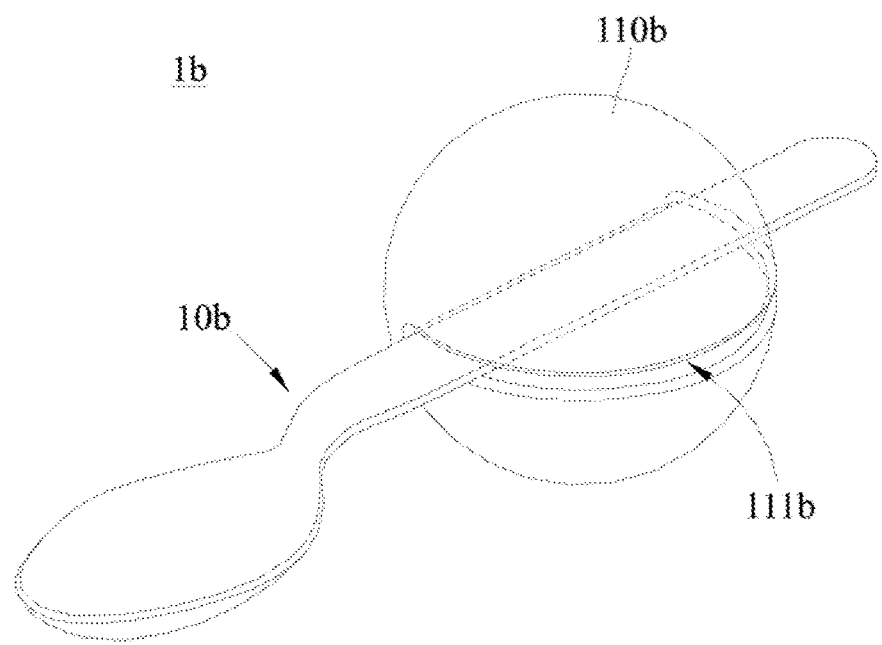
FIG. 11 is a schematic perspective side view of an anti-tremor tool according to an eleventh embodiment of the present invention.

FIG. 11 is a schematic side view of an anti-tremor tool according to an eleventh embodiment of the present invention. In this embodiment, the anti-tremor tool 1b includes a tool unit 10b and an anti-tremor device (not shown in FIG. 11), and the anti-tremor device includes a carrying portion 110b. The carrying portion 110b has a groove or a tool unit assembling structure 111b, and the tool unit 10b passes through the tool unit assembling structure 111b and is provided on the carrying portion 110b.

Figure 12:
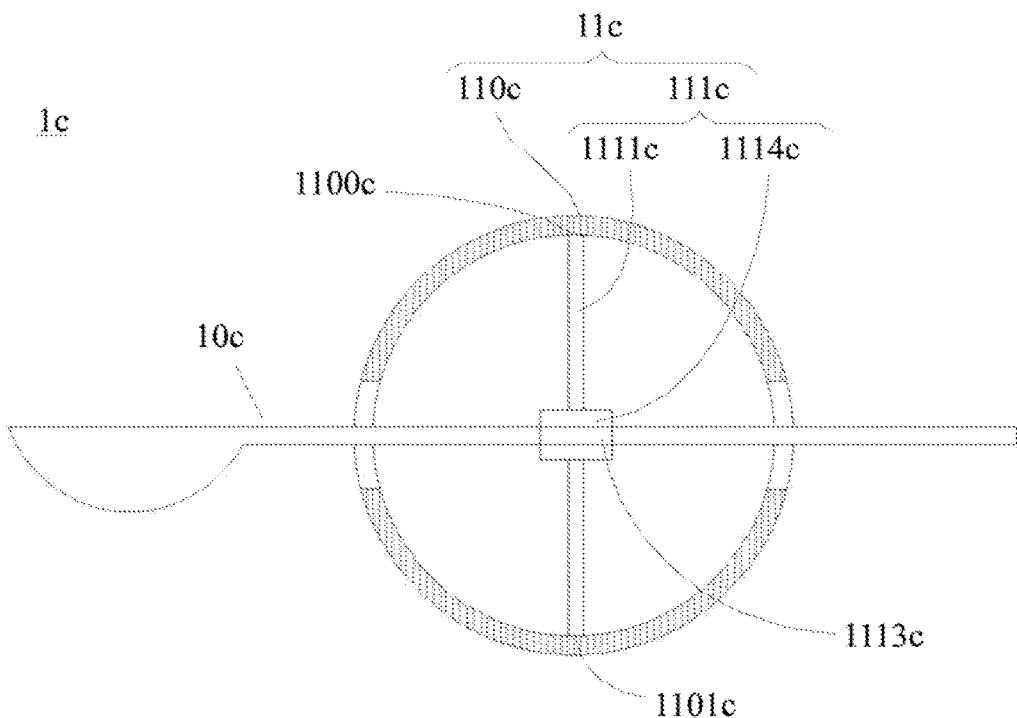
FIG. 12 is a schematic side sectional view of an anti-tremor tool according to a twelfth embodiment of the present invention.

FIG. 12 is a schematic side sectional view of an anti-tremor tool according to a twelfth embodiment of the present invention. In this embodiment, the anti-tremor tool 1c includes a tool unit 10c and an anti-tremor device 11c, and the anti-tremor device 11c includes a carrying portion 110c and an anti-tremor module 111c. The tool unit 10c and the carrying portion 110c are described in detail in the fourth embodiment, which will not be described in detail below. The anti-tremor module 111c includes an elastic body 1111c and a jointing portion 1114c. The opposite two ends or the periphery of the elastic body 1111c are respectively disposed on a top case portion 1100c and a bottom case portion 1101c of the carrying portion 110c, the tool unit 10c is supported by the elastic body 1111c through the jointing portion 1114c, and the jointing portion 1114c is mounted in the elastic body 1111c. In other embodiment, the jointing portion 1114c can also mount on the tool unit 10c. The jointing portion 1114c has a tool unit assembly structure 1113c, and the tool unit 10c is mounted in or connected to the anti-tremor module 111c through the tool unit assembly structure 1113c. The tool unit assembly structure 1113c is, for example, but not limited to, a tenon mechanism or a concave-convex structure. In other embodiment, a middle section of the elastic body 1111c can directly connect to the tool unit 10c, or can connect to the tool unit 10c through the jointing portion. The middle section of the elastic body 1111c is an area between the two opposite ends of the elastic body 1111c.

In addition, the jointing portion 1114c on the elastic body 1111c can be located exactly in the middle of the elastic body 1111c, that is, the distance between the jointing portion 1114c and the top case portion 1100c is substantially equal to the distance between the jointing portion 1114c and the bottom case portion 1101c. In another embodiment, the jointing portion 1114c on the elastic body 1111c can be relatively biased toward the top case portion 1100c, that is, the distance between the jointing portion 1114c and the top case portion 1100c is smaller than the distance between the jointing portion 1114c and the bottom case portion 1101c. Thereby, when the user uses the anti-tremor tool 1b, the jointing portion 1114c and the tool unit 10c coupled or mounted on the jointing portion 1114c can prevent too much downward due to gravity.

In another embodiment, a length of the jointing portion 1114c is greater than a length of the carrying portion 110c. The jointing portion 1114c is mounted in the carrying portion 110c, but not limited. The jointing portion 1114c can connect to the tool unit 10c through a corresponding connecting structure. For example, but not limit, the connecting structure may be a magnetic element or a columnar structure. In the embodiment, the tool unit 10c can only include the working end portion of the tool unit.

Figure 13:
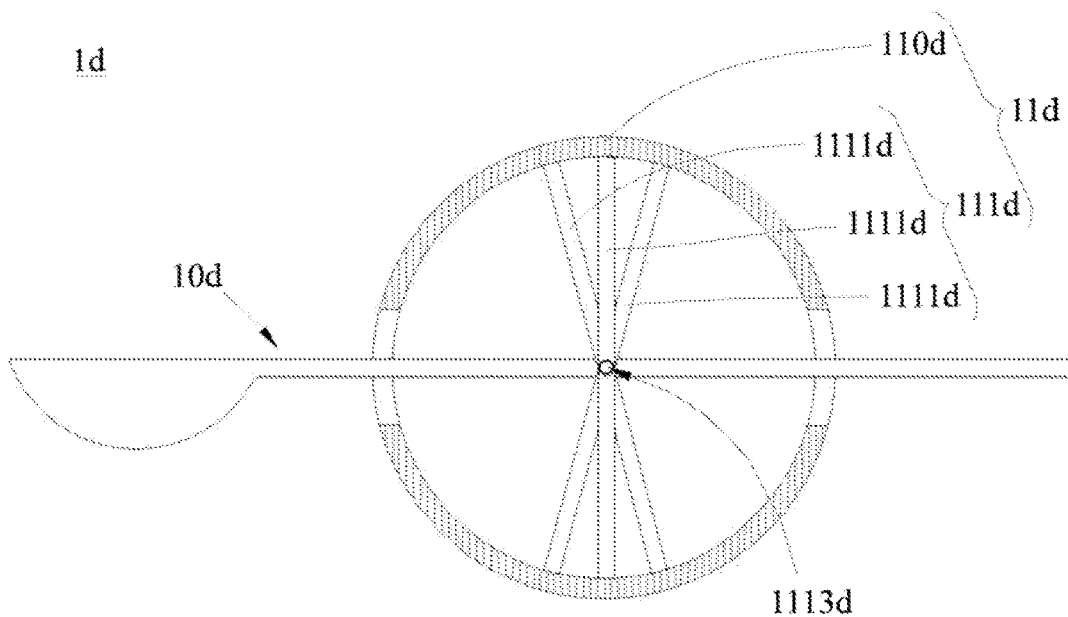
FIG. 13 is a schematic side sectional view of an anti-tremor tool according to a thirteenth embodiment of the present invention.

FIG. 13 is a schematic side sectional view of an anti-tremor tool according to a thirteenth embodiment of the present invention. In this embodiment, the anti-tremor tool 1d includes a tool unit 10d and an anti-tremor device 11d, and the anti-tremor device 11d includes a carrying portion 110d and an anti-tremor module 111d. The tool unit 10d and the carrying portion 10d are described in detail in the fourth embodiment, which will not be described below. The anti-tremor module 111d includes a plurality of elastic bodies 1111d. The elastic bodies 1111d cross each other or have an angled arrangement. The overlapping parts of these elastic bodies 1111d provide a tool unit assembly structure 1113d or a jointing portion (not shown), and the tool unit 10d is provided on or mounted in the anti-tremor module 111d through the tool unit assembly structure 1113d or the jointing portion. The tool unit assembly structure 1113d and the jointing portion are not limited to the small circle size of the FIG. 13, it could be any reasonable size and near the center.

Figure 14:
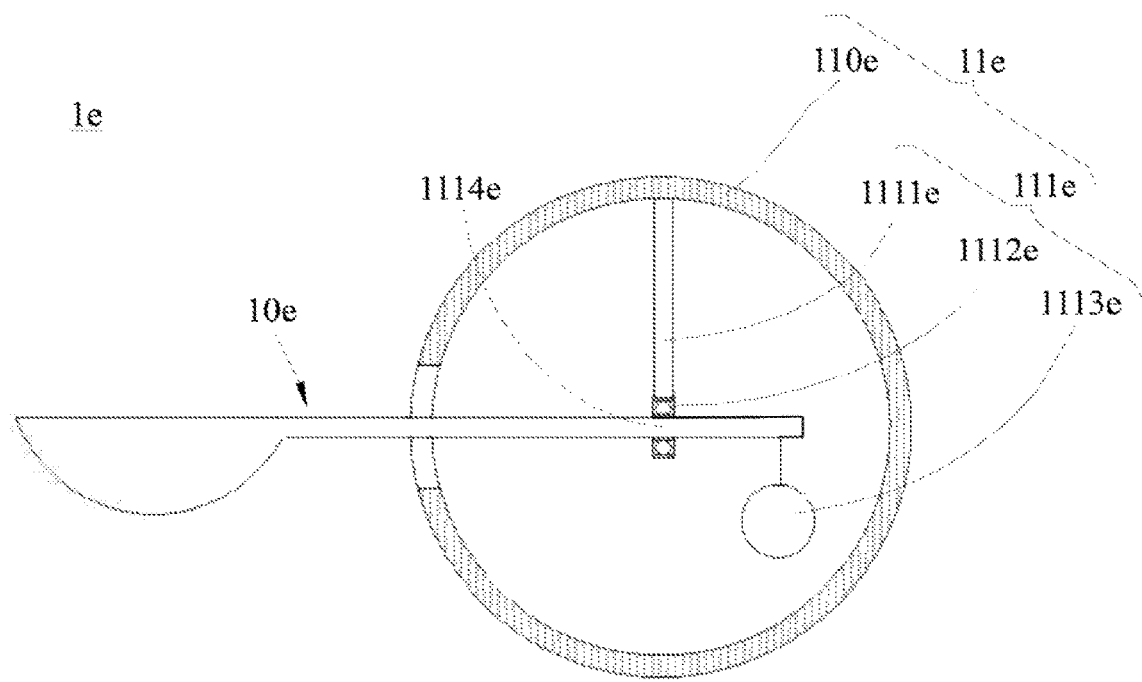
FIG. 14 is a schematic side sectional view of an anti-tremor tool according to a fourteenth embodiment of the present invention.

FIG. 14 is a schematic side sectional view of an anti-tremor tool according to a fourteenth embodiment of the present invention. In this embodiment, the anti-tremor tool 1e includes a tool unit 10e and an anti-tremor device 11e, and the anti-tremor device 11e includes a carrying portion 110e and an anti-tremor module 111e. The tool unit 10e and the carrying portion 110e are described in detail in the fourth embodiment, which will not be described below.

The anti-tremor module 111e includes a support portion 1111e, a bearing 1112e, and a counterweight 1113e. The support portion 1111e is, for example, a non-elastic rod or an elastic body, and is mounted in the carrying portion 110e. A bearing 1112e is provided on the support portion 1111e, and the bearing 1112e has a tool unit assembly structure 1114e. In detail, the bearing 1112e has an inner hole end and an outer end, wherein the outer end is provided at the support portion 1111e, and the hole at the inner hole end is the tool unit assembly structure 1114e. The tool unit 10e passes through the tool unit assembly structure 1114e and is provided on the anti-tremor module 111e. A counterweight 1113e is provided on the tool unit 10e so that the tool unit 10e is kept horizontal to reduce food spilling.

Figure 15:
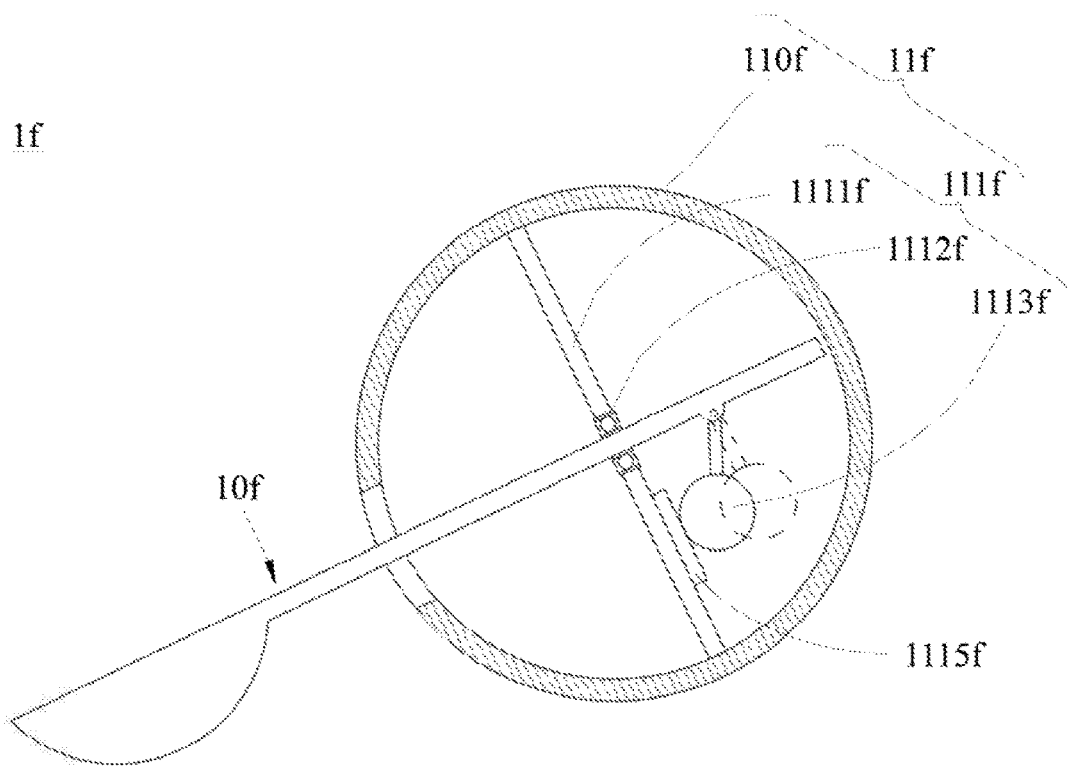
FIG. 15 is a schematic side sectional view of an anti-tremor tool according to a fifteenth embodiment of the present invention.

FIG. 15 is a schematic side sectional view of an anti-tremor tool according to a fifteenth embodiment of the present invention. In this embodiment, the anti-tremor tool 1f includes a tool unit 10f and an anti-tremor device 11f, and the anti-tremor device 111 includes a carrying portion 110f and an anti-tremor module 111f. The tool unit 10f and the carrying portion 110f are described in detail in the fourth embodiment, which will not be described in detail below.

In addition, the anti-tremor device 11f further includes a locking unit 1115f mounted on the support portion 1111f, and the counterweight 1113f is pivotally connected to the tool unit 10f. The lock unit 1115f and the counterweight 1113f have corresponding lock structures. When the carrying portion 110f is inclined toward the work end portion of the tool unit 10f, the counterweight 1113f will be rotated by gravity to contact the lock unit 1115f to restrict the rotation or movement of the tool unit 10f. Thereby, the tool unit 10f can be locked, and the user can conveniently operate the work end portion of the tool unit 10f, for example, but not limited to, getting food. In another embodiment, the bearing can be replaced by a hole. Further, the tool unit 10f can pivot on the carrying portion 110f through a pivot structure (not shown), and the more the pivot structures connecting to the tool unit, the stability of the tool unit will increase.

The carrying portion of the anti-tremor device or the handle portion of the tool unit can be additionally provided with other devices of various functions, such as a light, a display screen, a touch-sensitive operator, a button, a Bluetooth device, a multimedia player, and the like.

In the above-mentioned embodiments, the carrying portion of the anti-tremor device can be a spherical, cylindrical, annular cylinder, or any ergonomically designed shape, but the shape of the carrying portion is not limited to the above-mentioned shape. Further, the outer surface of the carrying portion can include a non-slip structure or a non-slip material to be easily gripped by the user, such as a bump structure, a matte structure, a non-slip material, silicone, rubber, and the like. Further, the support portion can directly or indirectly disposed or mounted in the carrying portion. The structure of the support portion can also integrally be formed with the carrying portion.

All technical features of the anti-tremor tool and the anti-tremor device of the invention can be configured in combination to achieve different degrees of anti-tremor effect or to add auxiliary operational functions.

In conclusion, the anti-tremor tool and the anti-tremor device disclosed in the present invention reduce or eliminate the vibration of the carrying portion by a novel electronic anti-tremor module or a mechanical anti-tremor module, thereby preventing the tool unit provided on the carrying portion from generating vibration, which helps people with tremor to eat on their own. The novel anti-tremor module of the anti-tremor device disclosed by the present invention can have a better anti-tremor effect than the conventional anti-tremor device.

Example Implementations

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

The systems, methods, and devices described herein each have several aspects, no single one of which is solely responsible for its desirable attributes. Without limiting the scope of this disclosure, several non-limiting features will now be discussed briefly. The following paragraphs describe various example implementations of the devices, systems, and methods described herein.

Example One: An anti-tremor tool, comprising: an anti-tremor device, comprising: a carrying portion, comprising at least one opening; at least one support portion, mounted in the carrying portion; wherein two ends or the periphery of the at least one support portion is connected to the carrying portion; and a tool unit; wherein one end of the tool unit is inserted through the at least one opening, and connects to the at least one support portion.

Example Two: The anti-tremor tool of Example One, wherein the tool unit is connected between a middle section of the at least one support portion, and the at least one support portion is at least one elastic body; and wherein the at least one elastic body is a single unit, and two ends or the periphery of the at least one elastic body is connected to the carrying portion.

Example Three: The anti-tremor tool of Example Two, wherein the at least one support portion of the anti-tremor device comprises a plurality of elastic bodies, the elastic bodies are arranged parallel to each other or have an angled arrangement, and two ends or the periphery of each of the elastic bodies is connected to the carrying portion; wherein the tool unit is connected to a middle section of each of the elastic bodies.

Example Four: The anti-tremor tool of Example One, wherein the at least one support portion of the anti-tremor device comprises: at least one frame body, rotatably mounted in the carrying portion, and connecting to the tool unit; and at least one elastic body or at least one shaft, mounted between the at least one frame body and the carrying portion.

Example Five: The anti-tremor tool of Example One, wherein the at least one support portion of the anti-tremor device comprises: a first frame body, rotatably mounted in the carrying portion; a second frame body, smaller than the first frame body, rotatably mounted in the first frame body, and connecting to the tool unit; at least one first elastic body or at least one first shaft, mounted between the first frame body and the carrying portion; and at least one second elastic body or at least one second shaft, mounted between the first frame body and the second frame body.

Example Six: The anti-tremor tool of Example Four, wherein the anti-tremor device further comprises: at least one elastic body, connecting to the tool unit, mounted in the at least one frame body, comprising two ends connecting to the at least one frame body, and comprising a middle section connecting to the tool unit.

Example Seven: The anti-tremor tool of Example Five, wherein the anti-tremor device further comprises: at least one elastic body, connecting to the tool unit, mounted in the second frame body, comprising two ends connecting to the second frame body, and comprising a middle section connecting to the tool unit.

Example Eight: The anti-tremor tool of Example One, wherein the at least one support portion includes: at least one elastic body; wherein one end of the at least one elastic body is connected to the carrying portion; a counterweight, connected to the other end of the at least one elastic body, and could slide or move relative to the carrying portion; and wherein the tool unit is supported by the counterweight or the at least one elastic body.

Example Nine: The anti-tremor tool of Example One, wherein the tool unit is supported by the at least one support portion, and is rotatable relative to the carrying portion; wherein the anti-tremor device further has a locking unit and a counterweight; wherein one of the locking unit and the counterweight is provided on the tool unit, and the other of the locking unit and the counterweight is provided on the at least one support portion or the carrying portion; wherein the counterweight can be rotated or moved relative to the carrying portion, and wherein when the carrying portion is inclined to a working end portion of the tool unit, the counterweight will rotate or move, and when the counterweight contacts the locking unit, the tool unit will be restricted from rotating or moving.

Example Ten: The anti-tremor tool of Example One, Two, Three, Four, Five, or Eight, wherein a connection area between the tool unit and the at least one support portion comprises: a tool unit assembly structure, comprising at least one magnetic unit, at least one elastic unit, at least one clamping unit, at least one hole, at least one bearing, at least one tenon, at least one bump structure, at least one tube structure, at least one thread structure, at least one columnar structure, at least one sawtooth structure, or a combination thereof.

Example Eleven: The anti-tremor tool of Example One, Two, Three, Four, Five, or Eight, wherein the tool unit is connected to the at least one support portion through a jointing portion; wherein the jointing portion comprises at least one magnetic unit, at least one elastic unit, at least one clamping unit, at least one hole, at least one bearing, at least one tenon, at least one bump structure, at least one tube structure, at least one threaded structure, at least one columnar structure, at least one sawtooth structure, or a combination thereof.

Example Twelve: The anti-tremor tool of any one of Examples One to Eleven, wherein a front end of the tool unit is a working end portion, and a rear end of the tool unit is a handle portion; wherein the handle portion comprises an extension section and an end section, and the extension section is formed between the working end portion and the end section; wherein the end section of the tool unit is bent downward, bolded, thickened, weighted, or the end section of the tool unit comprises a counterweight structure that is integrally formed with the tool unit, or movably mounted on the tool unit.

Example Thirteen: The anti-tremor tool of any one of Examples One to Twelve, wherein an area of a center of gravity of the tool unit or an extended section of a handle portion of the tool unit is connected to the at least one support portion.

Example Fourteen: The anti-tremor tool of any one of Examples One to Thirteen, wherein the anti-tremor device further includes at least one elastic film or at least one waterproof and dustproof film, which is disposed on the at least one opening of the carrying portion.

Example Fifteen: The anti-tremor tool of any one of Examples One to Fourteen, wherein the tool unit comprises at least one baffle, and the at least one baffle and the at least one opening are located on the same side of the at least one support portion, and a gap is located between the at least one baffle and the at least one opening.

Example Sixteen: The anti-tremor tool of any one of Examples One to Fifteen, wherein one surface of the carrying portion has an auxiliary structure, a thermoplastic material, or a non-slip material for better holding.

Example Seventeen: The anti-tremor tool of any one of Examples One to Sixteen, further comprising, an auxiliary holding portion, connected to the carrying portion; wherein the auxiliary holding portion can be moved, rotated relative to the carrying portion, or detachably connected to the carrying portion.

Example Eighteen: The anti-tremor tool of any one of Examples One to Seventeen, wherein the carrying portion has at least one second opening; and wherein the tool unit is inserted through the at least one opening and the at least one second opening.

Example Nineteen: The anti-tremor tool of any one of Examples One to Eighteen, wherein the tool unit is bent upward, downward, curved, or non-horizontal, or the tool unit has an adjustable length.

Example Twenty: The anti-tremor tool of any one of Examples One to Nineteen, further comprising at least one sensing circuit module mounted in the carrying portion or in an auxiliary holding portion connected to the carrying portion; wherein, the at least one sensing circuit module is used to calculate a Fourier transform formula, to measure or analyze different axial vibrations, to draw polygonal charts, to display the sensing data or result, to communicate signals with other devices, or to do a combination of the above.

Example Twenty One: The anti-tremor tool of any one of Examples One to Twenty, wherein a surface or an exterior of an auxiliary holding portion or the carrying portion is further provided with a decoration, a clamp, a magnetic body, a thermoplastic material, a non-slip material, an auxiliary structure, or a connection structure for attaching objects.

Example Twenty Two: An anti-tremor tool, comprising: a carrying portion, having at least two openings; a tool unit, inserted through the at least two openings of the carrying portion; and wherein the carrying portion is mounted on an extension section of a handle portion of the tool unit.

Example Twenty Three: The anti-tremor tool of Example Twenty Two, further comprising: at least one elastic body, and wherein the at least one elastic body is a single unit, and two ends or the periphery of the at least one elastic body is connected to the carrying portion; wherein the tool unit is connected to a middle section of the at least elastic body.

Example Twenty Four: An anti-tremor device, comprising: a carrying portion; an anti-tremor module, mounted in the carrying portion; and an auxiliary holding portion, connected to the carrying portion; wherein the auxiliary holding portion can be moved, rotated relative to the carrying portion, or detachably connected to the carrying portion.

Example Twenty Five: The anti-tremor device of Example Twenty Four, further comprising at least one sensing circuit module mounted in the carrying portion or in the auxiliary holding portion; wherein, the at least one sensing circuit module is used to calculate a Fourier transform formula, and to measure, record or analyze different axial vibrations, to draw polygonal charts, or to do a combination of the above.

Example Twenty Six: An anti-tremor device, comprising: a carrying portion, having a thermoplastic material, or at least one tool unit assembly structure for connecting a tool unit or an auxiliary holding portion; wherein the carrying portion has an anti-tremor module or at least one support portion; wherein two ends or a periphery end of the at least one supporting part is connected to the carrying portion.

Example Twenty Seven: The anti-tremor device of Example Twenty Six, comprising: a carrying portion, having a tool unit assembly structure for connecting the tool unit; an anti-tremor module, mounted in or supported by the carrying portion, and comprising: a counterweight; a motor, connected to the counterweight to drive the counterweight to rotate; a power source, electrically connected to the motor; and a power switch, for turning on or off an electrical connection between the power source and the motor; wherein the motor drives the counterweight to rotate relative to the carrying portion, or drives the counterweight and the power source to rotate relative to the carrying portion.

Example Twenty Eight: The anti-tremor device of Example Twenty Seven, wherein the anti-tremor module further comprises a circuit module that has a sensing unit, a processing unit, and a control unit; wherein the processing unit is coupled to the sensing unit, the control unit, the power source, and the motor; wherein the processing unit is activated when the sensing unit detects a tremor, otherwise the processing unit is deactivated to turn off the current of the motor; and wherein when the detected tremor is greater, the control unit accelerates the motor or increases the current of the motor.

Example Twenty Nine: The anti-tremor device of Example Twenty Seven, wherein the carrying portion includes: a first carrying portion; and a second carrying portion, detachably connected to the first carrying portion; wherein the counterweight is supported by or mounted in the first carrying portion, and one or both of the motor and the power source are mounted in the second carrying portion.

Example Thirty: An anti-tremor tool, comprising: a tool unit; and an anti-tremor device, comprising: a carrying portion, connecting a tool unit or having the assembly structure for detachably connecting the tool unit; an anti-tremor module, mounted in the carrying portion, and comprising: a counterweight; a motor, connected to the counterweight to drive the counterweight to rotate; a power source, electrically connected to the motor; and a power switch, for turning on or off an electrical communication between the power source and the motor; wherein the motor drives the counterweight to rotate relative to the carrying portion, or drives the counterweight and the power source to rotate relative to the carrying portion.

Example Thirty One: An anti-tremor device comprising: a carrying portion including: at least one opening; at least one support portion, provided in the carrying portion; wherein two ends or the periphery of the at least one support portion is connected to the carrying portion; and a jointing portion, connected to the at least one support portion, and having at least one magnetic member, at least one elastic member, at least one clamp, at least one hole, at least one bearing, at least one tenon, at least one concave-convex structure, at least one tube structure, at least one threaded structure, at least one columnar structure, at least one sawtooth structure, or a combination thereof; wherein the jointing portion is used for connecting to a tool unit.

Example Thirty Two: The anti-tremor device of Example Thirty One, wherein the jointing portion is connected to a middle section of the at least one support portion, and the at least one support portion is at least one elastic body, the at least one elastic body is a single component, and two ends or the periphery of the at least one elastic body is connected to the carrying portion.

Example Thirty Three: An auxiliary holding device, comprising: an auxiliary holding portion, having concave and convex grooves corresponding to human fingers, ergonomic structures, rubber, silicone, Velcro belts, or length adjustable belts; at least one sensing circuit module, mounted in the auxiliary holding portion; wherein the at least one sensing circuit module is used to calculate a Fourier transform formula, and to measure, record or analyze different axial vibrations, to draw polygonal charts, to display the sensing data or result, to communicate signals with other devices, or to do a combination of the above; an assembly structure, mounted on the auxiliary holding portion for connecting to an anti-tremor device or an anti-tremor tool.

As noted above, implementations of the described examples provided above may include hardware, a method or process, and/or computer software on a computer-accessible medium.

Additional Implementation Considerations

Various embodiments of various disease altering devices and methods, have been disclosed herein. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The foregoing description and examples have been set forth to illustrate the disclosure according to various embodiments and are not intended as being unduly limiting. The headings provided herein are for organizational purposes only and should not be used to limit embodiments. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. References cited herein are incorporated by reference in their entirety. The description of an embodiment as "preferred" does not limit the use or scope of alternative embodiments.

While the methods and devices described herein may be susceptible to various modifications and alternative forms, specific examples thereof have been shown in the drawings and are herein described in detail. It should be understood, however, that the embodiments disclosed should cover modifications, equivalents, and alternatives falling within the spirit and scope of the various embodiments described herein and the appended claims.

Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some examples, acts or events can be performed concurrently, e.g., through multi-threaded processing, interrupt processing, or multiple processors or processor cores or on other parallel architectures, rather than sequentially.

The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular embodiment.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 hour" includes "1 hour." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C. or A, B, and C.

When a feature or element is herein referred to as being "on" another feature or element, it may be directly on the other feature or element or intervening features and/or elements may also be present. In contrast, when a feature or element is referred to as being "directly on" another feature or element, there may be no intervening features or elements present. It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present.

Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features due to the inverted state. Thus, the term "under" may encompass both an orientation of over and under, depending on the point of reference or orientation. The device may be otherwise oriented (rotated 90 degrees or at other orientations) and the spatially relative descriptors used herein interpreted accordingly. Similarly, the terms "upwardly", "downwardly", "vertical", "horizontal" and the like may be used herein for the purpose of explanation only unless specifically indicated otherwise.

Although the terms "first" and "second" may be used herein to describe various features/elements (including steps or processes), these features/elements should not be limited by these terms as an indication of the order of the features/elements or whether one is primary or more important than the other, unless the context indicates otherwise. These terms may be used to distinguish one feature/element from another feature/element. Thus, a first feature/element discussed could be termed a second feature/element, and similarly, a second feature/element discussed below could be termed a first feature/element without departing from the teachings provided herein.

Although various illustrative embodiments have been disclosed, any of a number of changes may be made to various embodiments without departing from the teachings herein. For example, the order in which various described method steps are performed may be changed or reconfigured in different or alternative embodiments, and in other embodiments one or more method steps may be skipped altogether. Optional or desirable features of various device and system embodiments may be included in some embodiments and not in others. Therefore, the foregoing description is provided primarily for the purpose of example and should not be interpreted to limit the scope of the claims and specific embodiments or particular details or features disclosed.

The examples and illustrations included herein show, by way of illustration and not of limitation, specific embodiments in which the disclosed subject matter may be practiced. As mentioned, other embodiments may be utilized and derived therefrom, such that structural and logical substitutions and changes may be made without departing from the scope of this disclosure. Such embodiments of the disclosed subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve an intended, practical or disclosed purpose, whether explicitly stated or implied, may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. An anti-tremor tool comprising:
a tool unit having a working end portion and a handle having a first handle end connected to the working end portion and a second handle end opposite to the first handle end, the handle defining a first longitudinal axis, an anti-tremor device comprising a hollow substantially spherical carrying portion and a single elastic body body, the elastic body defining a second longitudinal axis and having two body ends, the elastic body is inside the carrying portion so that each of the two body ends are respectively engaged to opposite inner sides of the carrying portion, the carrying portion has two opposing openings to receive the handle of the tool unit in a way that the first handle end and the second handle end are outside the carrying portion and a middle portion of the handle is inside the carrying portion, and the middle portion of the handle is mounted in or connected to the elastic body so that the first longitudinal axis is substantially perpendicular to the second longitudinal axis.

2. The anti-tremor tool as claimed in claim 1, the tool unit is a spoon and the working end portion is a spoon bowl.

3. The anti-tremor tool as claimed in claim 1, the middle portion of the handle is mounted in or connected to a middle of the elastic body.

4. The anti-tremor tool as claimed in claim 1, the first handle end includes a baffle adjacent one of the openings in the carrying portion.

5. The anti-tremor tool as claimed in claim 4, the baffle is larger than the one of the openings in the carrying portion.

6. The anti-tremor tool as claimed in claim 1, the elastic body is a spring.

7. An anti-tremor tool comprising: a tool unit having a working end and a handle connected to the working end, an anti-tremor device comprising a spherical carrying portion and an anti-tremor module, the carrying portion has at least one opening to receive the handle of the tool unit, the anti-tremor module having a power source, a control module, and a motor supported inside the carrying portion, the anti-tremor module having a counter weight rotatably supported inside the carrying portion, the control module is engaged with the power source and the motor, the power source is electrically connected to the motor and the control module, and the motor extends through the handle of the tool unit to engage the counter weight in order to drive the counter weight to rotate relative to the carrying portion.

8. The anti-tremor tool as claimed in claim 7, an outside surface of the carrying portion has an auxiliary structure, a thermoplastic material, or a non-slip material to assist in gripping the carrying portion.

9. The anti-tremor tool as claimed in claim 7, the at least one opening in the carrying portion is two openings and the handle is received in both of the openings.

10. The anti-tremor tool as claimed in claim 7, the control module comprises a storage unit, a sensing unit, a processing unit, and a control unit.

11. The anti-tremor tool as claimed in claim 7, the tool unit is a spoon and the working end is a spoon bowl.

* * * * *